US009587242B2

(12) United States Patent
Bodie et al.

(10) Patent No.: US 9,587,242 B2
(45) Date of Patent: Mar. 7, 2017

(54) FILAMENTOUS FUNGI HAVING AN ALTERED VISCOSITY PHENOTYPE

(75) Inventors: Elizabeth A. Bodie, San Carlos, CA (US); Robert James Pratt, II, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 77 days.

(21) Appl. No.: 14/113,930

(22) PCT Filed: Apr. 20, 2012

(86) PCT No.: PCT/US2012/034399
§ 371 (c)(1),
(2), (4) Date: Apr. 10, 2014

(87) PCT Pub. No.: WO2012/145592
PCT Pub. Date: Oct. 26, 2012

(65) Prior Publication Data
US 2014/0220689 A1 Aug. 7, 2014

Related U.S. Application Data

(60) Provisional application No. 61/478,160, filed on Apr. 22, 2011, provisional application No. 61/478,162, filed on Apr. 22, 2011, provisional application No. 61/480,602, filed on Apr. 29, 2011, provisional application No. 61/480,610, filed on Apr. 29, 2011, provisional application No. 61/480,629, filed on Apr. 29, 2011.

(51) Int. Cl.
C12N 1/00 (2006.01)
C12N 15/79 (2006.01)
C12N 1/14 (2006.01)
C12N 15/80 (2006.01)
C12N 1/36 (2006.01)
C12N 9/24 (2006.01)

(52) U.S. Cl.
CPC ............... *C12N 15/79* (2013.01); *C12N 1/14* (2013.01); *C12N 1/36* (2013.01); *C12N 9/2405* (2013.01); *C12N 15/80* (2013.01)

(58) Field of Classification Search
CPC ..................................................... C12N 15/79
See application file for complete search history.

(56) References Cited

U.S. PATENT DOCUMENTS 7,371,581 B2 * 5/2008 Gunnewijk et al. ......... 436/161
2004/0224388 A1 11/2004 Dunn-Coleman

FOREIGN PATENT DOCUMENTS

WO    WO 01/09352      2/2001
WO    WO 2005/001036   1/2005

OTHER PUBLICATIONS

Atschul et al., "Basic local alignment search tool," (J. Mol. Biol. 215:403-10)(1990).
Atschul et al., "Local Alignment Statistics," Meth. Enzymol. 266:460-80 (1993).
Dai et al., "Identification of genes associated with morphology in Aspergillus niger by using supression subtractive hybridization," Applied and Environmental Microbiolyg, ol. 70, No. 4, pp. 2474-2485 (2004).
Devereux et al., "A comprehensive set of sequence analysis programs for the VAX," Nucleic Acids Res. 12:387-95 (1984).
Feng et al., "Progressive Sequence Alignment as a Prerequisite to Correct Phytogenetic Trees," J. Mol. Evol. 35:351-60 (1987).
Garcia et al., "The Global Transcriptional Response to Transient Cell Wall Damage in *Saccharomyces cerevisiae* and its Regulation by the Cell Integrity Signaling Pathyway," J. Biol. Chem. 279-15183-15195 (2004).
Henikoff et al., "Amino acid substitution matrices from protein blocks," Proc. Natl. Acad. Sci. USA 89:10915) (1989).
Higgins et al., "CLUSTAL: a package for performing multiple sequence alignment on a micrcomputer," Gene 73:237-244) (1988).
Higgins et al., "Fast and sensititve multple sequence alignments on a microcomputer," CABIOS Communication, 5:151-53 (1989).
Hughes et al.. "Assembly, organization, and function of the COPII coat." Cell. Biol. 129-51 (2008).
International Search Report for WO2012145592 (PCT/US2012/034399), 5 pages, published Oct. 26, 2012.
Karababa et al., "CRZ1, a target of the calcineurin pathway in Candida albicans," Mol. Microiol. 59:1429-1451 (2006).
Karhinen, L. et al., "Endoplasmic Reticulum Exit of a Secretory Glycoprotein in the Absence of Sec24p Family Proteins in Yeast," Traffic 6:562-74 (2005).
Karlin et al., "Applications and statistic for multiple high-scoring segments in molecular sequences,"(Proc. Natl. Acad. Sci. USA 90:5873-87) (1993).
Kothe, G., Calcineurin Subunit B is Required for Normal Vegetative Growth in Neurospora crassa, Fungal Genet Biol 23:248-258 (1998).
Lagorce et al., "Genome wide analysis of the response to cell wall mutation in the yeast *S.cerevisiae*," J. Biol Chem. 278:20345-20357 (2003).
Marx et al., "Cloning, disruption and protein secretory phenotype of the GAS1 homologue of Pichia pastoris," FEMS Microbiology Letters, vol. 284, No. 1, pp. 40-47 (2006).
Mouyna, I. et al., "Deletion of GEL2 encoding for a β(1-3)glucanosyltransferase affects morphogenecic and virulence in Aspergillus lurnigatus," Molecular Microbiol 56(6), 1675-1688 (2005).
Munro, C et al., "The PKC, HOG and Ca2+ signalling pathways co-ordinately regulate chitin synthesis in Candida allicans." Mol. Microbiol. 63:1399-1413, (2007).
Needleman et al., "A General Method Applicable to the Search for Similarities in th eAmino Acid Sequence of Two Proteins," J. Mol. Biol., 48:443 (1970).

(Continued)

Primary Examiner — Albert Navarro
(74) Attorney, Agent, or Firm — Danisco US Inc.

(57) ABSTRACT

Described are compositions and methods relating to variant filamentous fungi having altered growth characteristics. Such variants are well-suited for growth in submerged cultures, e.g., for the large-scale production of enzymes and other proteins for commercial applications.

30 Claims, 1 Drawing Sheet

(56) References Cited

OTHER PUBLICATIONS

Pardini et al., "The CRH Family Coding for Cell Wall Glycosylphosphatidylinositol Proteins with a Predicted Transglycosidase Domain Affects Cell Wall Organization and Virtulence of Candida albicans," J. Biol. Chem. 281:40399-40411 (2006).

Passolunghi, S. et al., "Cloning of Zygosaccharomyces bailii GAS1 homologue and effect of cell wall engineering on protein secretory phenotype," Microbial Cell Factories 9:7-17 (2010).

Pearson et al., Improved tools for biological sequence comparison, Proc. Natl. Acad. Sci. USA 85:2444 (1988).

Peng, R. et al., "Evidence for Overlapping and Distinct Functions in Protein Transport of Cost Protein Sec24p Family Members," J. Biol. Chem. 275:11521-28 (2000).

Peterbauer, C. et al., "The Tricoderma atroviride seb1 (stress response element binding) gene encodes an AGGGG-binding protein which is involoved in the response to high osmolarity stress," (Molecular Genetics and Genomics 268:223-31) (2002).

Popolo et al., "Disulfide Bond Structure and Domain Organization of Yeast (1,3)-Glucanosyltransferases Involved in Cell Wall Biogenesis," J Biol. Chem., vol. 283, No. 27, pp. 18553-18565 (2008).

Prokisch. H., et al., "Impairmenet of calcineurin function in Neurospora crassa reveals its essential role in hyphal growth, morphology and maintenance of the apical Ca2+ gradient," Mol. Gen. Genet. 256:104-114 (1997).

Roberg, K.J. et al., "*LST1* is a *SEC24* Homologue Used for Selective Export of the Plasma Membrane ATPase from the Endoplasmic Reticulum." J. Cell. Biol. 145:659-72 (1999).

Schirawski, J. et al. "Endoplasmic reticulum glucosidase II is required for pathogenicity of *Ustilago aydis*," (2005).

Shimoni, Y. et al., "Lstip and Sec24p Cooperate in Sorting of the Plasma Membrane ATPase into COPII Vesicles in *Saccharomyces cerevisiae*," J. Cell. Biol. 151:973-84 (2000).

Simola, M et al. "Trehalose is required for conformational repair of heat denatured proteins in the yeast endoplasmic reticulum but not for maintenance of membrane traffic functions after severe heat stress," Molecular Microbiology 37(1): 42-53 (2000).

Singer, M et al., Multiple Effects of Trehalose on Protein Folding In Vitro and In Vivo, Molecular Cell, vol. 1, 639-648, Apr. 1998.

Smith et al. "Comparison of Biosequences," Adv. Appl. Math. 2:482 (1981).

Turchini, A, et al., Increase of External Osmolarity Reduces Morphogenetic Defects and Accumulation of Chitin in a gas1 Mutatn of *Saccharomyces cerevisiae*J. Bacteriol. 182:1167-71 (2000).

Yamazaki et al., "A chitinase gene, chiB, involved in the autolytic process of Asperigillus nidulans," Current Genetics, vol. 51, No. 2, pp. 89-98 (2007).

Yoshimoto et al., "Genome-wide Analysis of Gene Expression Regulated by the Calcineurin/Crz1p Signaling Pathway in *Saccharomyces cerevisiae*," J. Biol. Chem. 227:31079-31088 (2002).

\* cited by examiner

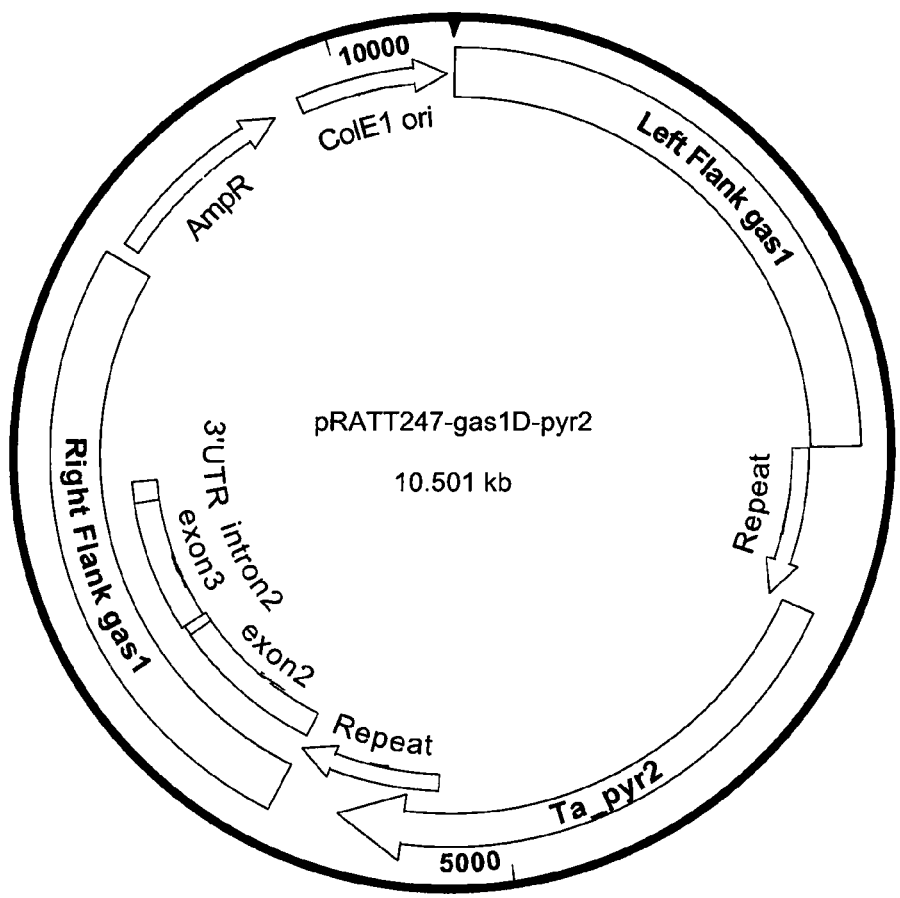

SEQUENCE LISTING

<160> NUMBER OF SEQ ID NOS: 12

<210> SEQ ID NO 1
<211> LENGTH: 540
<212> TYPE: PRT
<213> ORGANISM: Trichoderma reesei

<400> SEQUENCE: 1

Met Ser Leu Ser Lys Leu Ser Val Ser Leu Leu Ala Leu Ala Gly Ser
1               5                   10                  15

Ala Ile Ala Gly Asp Leu Pro Ser Ile Thr Ala Lys Gly Ser Lys Phe
            20                  25                  30

Phe Tyr Pro Asn Gly Thr Gln Phe Ile Lys Gly Val Ala Tyr Gln
        35                  40                  45

```
Gln Asp Val Gly Gln Ala Gly Ser Thr Asp Ser Ser Thr Ser Thr Phe
     50                  55                  60
Ile Asp Pro Leu Ser Ser Glu Ala Asn Cys Lys Arg Asp Val Pro Leu
 65                  70                  75                  80
Leu Lys Gln Leu Gly Thr Asn Val Ile Arg Thr Tyr Ala Ile Asp Pro
                 85                  90                  95
Lys Ala Asp His Ser Ala Cys Met Lys Leu Leu Asn Asp Ala Gly Ile
            100                 105                 110
Tyr Val Phe Ser Asp Leu Gly Glu Pro Ser Leu Ser Ile Asn Arg Asp
            115                 120                 125
Thr Pro Ala Trp Asn Thr Glu Leu Phe Asp Arg Tyr Lys Ala Val Val
        130                 135                 140
Asp Glu Met Ser Gln Tyr Pro Asn Val Ile Gly Tyr Phe Ala Gly Asn
145                 150                 155                 160
Glu Val Ser Asn Ala Lys Asn Asn Thr Gly Ala Ser Ala Tyr Val Lys
                165                 170                 175
Ala Ala Val Arg Asp Thr Lys Ala Tyr Ile Lys Ser Lys Lys Tyr Arg
            180                 185                 190
Trp Gln Gly Val Gly Tyr Ala Ala Asn Asp Asp Val Asp Ile Arg Ala
        195                 200                 205
Glu Ile Ala Asp Tyr Phe Asn Cys Gly Asp Gln Asp Glu Ala Ile Asp
210                 215                 220
Phe Trp Gly Tyr Asn Ile Tyr Ser Trp Cys Gly Gln Ser Ser Met Gln
225                 230                 235                 240
Lys Ser Gly Tyr Asp Glu Gln Thr Thr Phe Phe Ser Asn Tyr Ser Val
                245                 250                 255
Pro Val Phe Phe Ala Glu Tyr Gly Cys Asn Leu Pro Ser Gly Ala Ala
            260                 265                 270
Ala Arg Ile Phe Gln Glu Thr Ala Ala Leu Tyr Ser Asp Glu Met Thr
        275                 280                 285
Lys Val Phe Ser Gly Gly Ile Val Tyr Met Tyr Phe Glu Glu Asp Asn
290                 295                 300
Asp Tyr Gly Leu Val Lys Val Asn Asn Gly Ala Val Ser Lys Leu Lys
305                 310                 315                 320
Asp Phe Ser Ala Leu Gln Thr Gln Val Thr Lys Ala Asp Pro Lys Gly
            325                 330                 335
Val Asp Ala Asp Asp Tyr Lys Pro Thr Asn Lys Pro Ala Ser Cys Pro
        340                 345                 350
Ala Leu Thr Asp Asp Trp Gln Ala Ile Asn Ser Leu Pro Pro Thr Pro
            355                 360                 365
Asp Ala Ser Leu Cys Thr Cys Met Gln Ser Ser Leu Ser Cys Val His
        370                 375                 380
Ala Asp Asp Leu Asp Thr Lys Asp Phe Gly Asp Ile Phe Gly Phe Ile
385                 390                 395                 400
Cys Gly Lys Ser Pro Glu Val Cys Ala Gly Ile Asn Gly Asp Pro Ser
                405                 410                 415
Thr Gly Val Tyr Gly Ala Tyr Ser Met Cys Glu Asp Ala Ala Lys Leu
            420                 425                 430
Asp Tyr Val Leu Asp Ala Tyr Tyr Gln Ser Gln Lys Lys Ala Ser Thr
            435                 440                 445
Ala Cys Asp Phe Asn Gly Gln Ala Gln Val Val Ser Pro Lys Ala Ala
450                 455                 460
Ser Thr Cys Ser Ala Ala Leu Ala Ser Ala Ser Ala Ile Asn Lys Gln
```

```
            465                 470                 475                 480
Ala Ala Thr Ala Thr Ala Pro Val Gly Ala Gly Ser Thr Ser Gly Ser
                    485                 490                 495

Lys Gly Ala Ala Thr Ser Thr Asn Ala Ala Val Ala Gly Arg Pro Val
                500                 505                 510

Ser His Leu Leu Ser Met Gly Glu Ile Ser Val Ala Leu Tyr Met Gly
                515                 520                 525

Val Ala Met Leu Ala Gly Gly Ala Met Ile Val Leu
                530                 535                 540

<210> SEQ ID NO 2
<211> LENGTH: 539
<212> TYPE: PRT
<213> ORGANISM: Fusarium oxysporum

<400> SEQUENCE: 2

Met Lys Phe Ser Ala Ala Ile Val Ala Ala Ala Thr Ala Ala Ser
1               5                  10                  15

Ala Lys Leu Glu Pro Ile Thr Met Lys Gly Ser Lys Leu Phe Tyr Ser
                20                  25                  30

Asn Gly Thr Gln Phe Phe Met Lys Gly Val Ala Tyr Gln Gln Asp Thr
                35                  40                  45

Ala Ala Ala Gly Glu Thr Asn Asp Lys Thr Thr Lys Tyr Ile Asp Pro
        50                  55                  60

Leu Ala Asp Glu Glu Ala Cys Lys Arg Asp Ile Pro Leu Leu Lys Gln
65                  70                  75                  80

Leu Gly Thr Asn Ile Ile Arg Thr Tyr Ala Ile Asn Pro Lys Ala Asp
                85                  90                  95

His Lys Ala Cys Met Lys Leu Leu Asp Ala Gly Ile Tyr Val Ile Ser
                100                 105                 110

Asp Leu Ser Glu Pro Ser Val Ser Ile Asn Arg Asp Asp Pro Lys Trp
                115                 120                 125

Asp Val Glu Leu Tyr Glu Arg Tyr Ile Gly Val Val Asp Glu Leu Gly
                130                 135                 140

Gln Tyr Asp Asn Val Val Gly Phe Phe Ala Gly Asn Glu Val Ser Asn
145                 150                 155                 160

Asn Val Ser Asn Thr Gln Ala Ser Ala Phe Val Lys Ala Ala Val Arg
                165                 170                 175

Asp Thr Lys Lys His Ile Lys Ser Lys Phe Ser Arg Trp Leu Gly Val
                180                 185                 190

Gly Tyr Ala Ser Asn Asp Asp Val Asp Ile Arg Glu Gln Ile Ala Asp
                195                 200                 205

Tyr Phe Asn Cys Gly Asp Asp Ser Arg Ile Asp Tyr Trp Gly Tyr
                210                 215                 220

Asn Ile Tyr Ser Trp Cys Gly Lys Ser Ser Met Gln Asp Ser Gly Tyr
225                 230                 235                 240

Ser Asp Gln Ala Lys Phe Phe Glu Asp Tyr Ser Val Pro Val Phe Phe
                245                 250                 255

Ala Glu Tyr Gly Cys Asn Glu Pro Asp Gly Ala Ala Gly Arg Ile Phe
                260                 265                 270

Asp Glu Thr Thr Ala Leu Tyr Glu Glu Lys Val Met Thr Asp Val Phe
                275                 280                 285

Ser Gly Gly Ile Val Tyr Met Tyr Phe Gln Glu Ala Asn Asp Tyr Gly
                290                 295                 300
```

-continued

```
Leu Val Lys Ile Ser Lys Asn Gly Asp Ala Val Lys Gln Lys Asp Phe
305                 310                 315                 320

Ala Gln Leu Gln Lys Lys Ala Asn Ala Ala Lys Pro Ser Gly Val Glu
            325                 330                 335

Glu Asp Ser Tyr Lys Pro Thr Gly Lys Ala Ala Thr Cys Pro Glu Gln
                340                 345                 350

Ser Lys Asn Trp Lys Ala Asn Ser Val Leu Pro Pro Val Pro Asp Ser
            355                 360                 365

Asp Leu Cys Asp Cys Met Val Lys Ser Arg Ser Cys Val Pro Ala Asp
        370                 375                 380

Asn Leu Lys Ala Lys Asp Phe Asn Asp Ile Phe Gly Tyr Ile Cys Gly
385                 390                 395                 400

Gln Asp Lys Lys Ile Cys Thr Ala Ile Asn Ala Asn Ala Thr Ala Gly
            405                 410                 415

Ile Tyr Gly Ala Tyr Ser Met Cys Ser Asn Glu Ala Lys Leu Ala Tyr
        420                 425                 430

Ile Leu Asp Ala Tyr Tyr Thr Ser Gln Lys Ser Ala Ala Asp Ala Cys
            435                 440                 445

Asp Phe Lys Gly Lys Ala Thr Thr Gln Lys Ala Glu Ser Gln Asp Ser
450                 455                 460

Cys Lys Ser Ala Leu Ala Ser Ala Ser Lys Ile Asn Glu Glu Val Ala
465                 470                 475                 480

Thr Ala Thr His Ala Val Ala Ser Ser Ser Thr Gly Gly Ser Asn Ser
            485                 490                 495

Ser Ser Glu Asp Asp Glu Asn Phe Gly Leu Gln Ala Ala Ser Ile Ala
        500                 505                 510

Arg Val Phe Ser Leu Gly Asp Phe Ala Val Gly Ala Tyr Met Ala Val
            515                 520                 525

Ala Gly Val Val Gly Ala Gly Met Val Leu Leu
        530                 535

<210> SEQ ID NO 3
<211> LENGTH: 530
<212> TYPE: PRT
<213> ORGANISM: Aspergillus niger

<400> SEQUENCE: 3

Met Lys Leu Ser Leu Ala Val Gly Ala Ala Leu Met Gly Ser Ala Leu
1               5                   10                  15

Ala Val Asp Ile Asp Pro Ile Val Ile Lys Gly Ser Lys Phe Phe Tyr
            20                  25                  30

Ser Ser Asn Asn Thr Gln Phe Tyr Ile Arg Gly Val Ala Tyr Gln Asp
        35                  40                  45

Asp Tyr Thr Gly Asn Ser Ser Gly Tyr Thr Asp Pro Leu Ala Asn
    50                  55                  60

Pro Thr Leu Cys Lys Arg Asp Ile Pro Ile Leu Gln Glu Leu Asn Thr
65                  70                  75                  80

Asn Val Ile Arg Val Tyr Ala Ile Asp Pro Thr Lys Asp His Thr Thr
            85                  90                  95

Cys Met Asn Leu Leu Ala Ala Ala Gly Ile Tyr Val Ile Ser Asp Leu
        100                 105                 110

Ser Asp Pro Thr Gln Ser Ile Asp Arg Ser Asp Pro Thr Trp Glu Thr
    115                 120                 125

Ser Leu Tyr Thr Arg Tyr Thr Asn Val Ile Asp Glu Leu Ile Gln Tyr
130                 135                 140
```

Asn Asn Thr Leu Ala Phe Phe Ala Gly Asn Glu Val Ser Asn Asp Val
145                 150                 155                 160

Ala Thr Thr Asp Ala Ser Ala Phe Val Lys Ala Val Arg Asp Met
            165                 170                 175

Lys Ala Tyr Ile Lys Ser Gln Gly Tyr Arg Ser Ile Gly Val Gly Tyr
                180                 185                 190

Ala Thr Asn Asp Asp Ser Asp Ile Arg Val Asn Met Ala Asp Tyr Phe
            195                 200                 205

Asn Cys Gly Ser Glu Asp Glu Ser Ile Asp Phe Trp Gly Tyr Asn Ile
            210                 215                 220

Tyr Ser Trp Cys Gly Asp Ser Ser Tyr Thr Lys Ser Gly Tyr Asp Glu
225                 230                 235                 240

Arg Thr Glu Glu Phe Arg Asn Tyr Ser Val Pro Val Phe Phe Ser Glu
                245                 250                 255

Tyr Gly Cys Asn Thr Val Gln Pro Arg Lys Phe Thr Asp Ile Lys Ala
            260                 265                 270

Leu Phe Gly Asp Gln Met Asn Asp Val Trp Ser Gly Ile Val Tyr
            275                 280                 285

Met Tyr Phe Gln Thr Asp Asn Asp Tyr Gly Leu Val Ser Ala Ile Asp
            290                 295                 300

Ser Thr Ser Val Ser Lys Leu Ala Asp Phe Thr Tyr Tyr Ser Ser Gln
305                 310                 315                 320

Ile Ala Ser Ala Thr Pro Ser Gly Thr Asn Lys Ala Ser Tyr Thr Pro
                325                 330                 335

Thr Asn Thr Ala Leu Gln Ser Cys Pro Ala Val Thr Ser Lys Ser Trp
            340                 345                 350

Leu Ala Thr Ser Ser Pro Leu Pro Pro Thr Pro Asn Gln Glu Leu Cys
            355                 360                 365

Thr Cys Met Asp Asn Ala Ser Gly Cys Val Val Lys Asp Ser Val Ser
        370                 375                 380

Ser Ser Asp Tyr Asp Asp Leu Phe Ser Thr Val Cys Gly Phe Thr Ser
385                 390                 395                 400

Cys Asp Gly Ile Phe His Asn Gly Thr Thr Gly Thr Tyr Gly Ala Tyr
                405                 410                 415

Ser Met Cys Gly Ala Lys Gln Gln Leu Asn Phe Val Leu Asp Lys Tyr
            420                 425                 430

Trp Lys Glu Gln Gly Lys Lys Ala Asp Ala Cys Gly Phe Asp Gly Ser
            435                 440                 445

Ala Thr Thr Ala Thr Val Lys Ala Thr Gly Thr Cys Ser Ala Leu
            450                 455                 460

Met Lys Glu Ala Gly Thr Ala Gly Thr Gly Thr Val Thr Ser Lys Pro
465                 470                 475                 480

Thr Gly Thr Ala Ala Gly Ser Ser Ser Ala Ser Gly Thr Gly Val
                485                 490                 495

Ser Ala Val Gly Ser Gly Ser Ala Ile Ile Ser Ile Gly Ala Trp Gln
            500                 505                 510

Val Gly Ala Tyr Val Val Thr Gly Val Val Ala Gly Leu Gly Met Val
            515                 520                 525

Leu Leu
530

<210> SEQ ID NO 4
<211> LENGTH: 538

<212> TYPE: PRT
<213> ORGANISM: Aspergillus oryzae

<400> SEQUENCE: 4

```
Met Lys Leu Ser Ser Ile Val Ala Gly Ala Ser Leu Phe Ala Ser Ser
1               5                   10                  15

Val Ile Ala Ala Asp Leu Asp Pro Ile Ile Lys Gly Ser Lys Phe
            20                  25                  30

Phe Tyr Lys Ser Asn Asp Thr Gln Phe Tyr Ile Arg Gly Val Ala Tyr
        35                  40                  45

Gln Gln Glu Tyr Ser Gly Pro Asp Ser Ser Ala Asn Ser Phe Lys Asp
    50                  55                  60

Pro Leu Ala Asp Ala Asp Ala Cys Lys Arg Asp Val Pro Tyr Leu Glu
65                  70                  75                  80

Lys Leu Gly Thr Asn Thr Ile Arg Val Tyr Ala Ile Asp Pro Lys Ser
                85                  90                  95

Asp His Lys Glu Cys Met Ser Leu Leu Ser Asp Ala Gly Ile Tyr Val
            100                 105                 110

Ile Ala Asp Leu Ser Ser Pro Gly Asp Ser Ile Asn Arg Asn Glu Pro
        115                 120                 125

Lys Trp Asp Asn Asp Leu Tyr Asn Arg Tyr Val Thr Val Val Asp Glu
130                 135                 140

Leu Ser Gln Tyr Ser Asn Val Ile Gly Phe Phe Ala Gly Asn Glu Val
145                 150                 155                 160

Ser Asn Ser Glu Asn Thr Thr Ser Ala Ser Ala Phe Val Lys Ala Ala
                165                 170                 175

Val Arg Asp Thr Lys Gln Tyr Ile Lys Ala Lys Asn Tyr Arg Ser Met
            180                 185                 190

Gly Val Gly Tyr Ala Thr Ser Asp Asp Ser Ser Ile Arg Lys Asn Met
        195                 200                 205

Ala Asn Tyr Phe Asn Cys Asn Gly Ala Asp Asp Ser Ile Asp Phe Trp
    210                 215                 220

Gly Tyr Asn Val Tyr Ser Trp Cys Gly Asp Ser Asn Tyr Glu Lys Ser
225                 230                 235                 240

Gly Tyr Ala Ser Arg Thr Glu Glu Phe Lys Asp Tyr Thr Val Pro Val
                245                 250                 255

Phe Phe Ala Glu Tyr Gly Cys Asn Ala Val Gln Pro Arg Lys Phe Thr
            260                 265                 270

Glu Val Gln Ala Leu Tyr Gly Asp Lys Met Ala Asp Val Trp Ser Gly
        275                 280                 285

Gly Ile Val Tyr Met Tyr Phe Gln Glu Glu Asn Asn Tyr Gly Leu Val
    290                 295                 300

Ser Val Asp Gly Asn Lys Val Ser Thr Lys Ala Asp Phe Ser Tyr Leu
305                 310                 315                 320

Ser Lys Glu Leu Ala Ser Ala Thr Pro Ser Gly Thr Lys Lys Gly Asp
                325                 330                 335

Tyr Gln Pro Thr Asn Thr Ala Leu Gln Ser Cys Pro Thr Val Asp Asp
            340                 345                 350

Lys Trp Leu Ala Thr Ser Ser Pro Leu Pro Ser Pro Asn Gln Asp
        355                 360                 365

Leu Cys Ser Cys Met Glu Glu Ser Leu Ser Ala Leu Lys Asp Lys
    370                 375                 380

Val Ser Gly Glu Gln Leu Asp Lys Leu Phe Gly Thr Val Cys Gly Tyr
385                 390                 395                 400
```

```
Asp Val Cys Asp Gly Ile Thr Thr Asn Ala Thr Thr Gly Lys Tyr Gly
                405                 410                 415

Ala Tyr Ser Val Cys Thr Pro Gln Gln Gln Leu Ser Tyr Ala Ile Asn
            420                 425                 430

Leu Tyr Tyr Gln Asn Gln Lys Ala Lys Gly Asn Gly Asp Lys Ala Cys
        435                 440                 445

Asp Phe Asn Gly Ala Ala Thr Thr Gln Ser Ser Lys Ser Gly Gly Ser
    450                 455                 460

Ala Cys Ser Ala Leu Leu Lys Glu Ala Gly Thr Ser Gly Thr Gly Thr
465                 470                 475                 480

Val Thr Ser Ser Pro Thr Gly Thr Ala Gly Ser Gly Ala Ser Asp Gly
                485                 490                 495

Ala Ala Ala Ser Ser Ser Gly Ser Ala Gly Gly Leu Val Ala Pro Ser
            500                 505                 510

Ser Val Asn Val Gly Ile Phe Gln Leu Gly Ala Tyr Val Val Thr Ala
        515                 520                 525

Met Val Ala Gly Ala Gly Met Ile Val Leu
    530                 535

<210> SEQ ID NO 5
<211> LENGTH: 540
<212> TYPE: PRT
<213> ORGANISM: Gibberella moniliformis

<400> SEQUENCE: 5

Met Lys Phe Ser Ala Ala Ile Val Ala Ala Ala Ala Thr Ala Ala Ser
1               5                   10                  15

Ala Lys Leu Glu Pro Ile Thr Met Lys Gly Ser Lys Leu Phe Tyr Ser
            20                  25                  30

Asn Gly Thr Gln Phe Phe Met Lys Gly Val Ala Tyr Gln Gln Asp Thr
        35                  40                  45

Ala Ala Ala Gly Gln Thr Asn Thr Lys Glu Thr Lys Tyr Ile Asp Pro
    50                  55                  60

Leu Ala Asp Glu Asp Ala Cys Lys Arg Asp Ile Pro Leu Leu Lys Gln
65                  70                  75                  80

Leu Gly Thr Asn Ile Ile Arg Thr Tyr Ala Ile Asp Pro Thr Ala Asp
                85                  90                  95

His Lys Ala Cys Met Lys Leu Leu Asp Asp Ala Gly Ile Tyr Val Ile
            100                 105                 110

Ser Asp Leu Ser Glu Pro Ser Val Ser Ile Asn Arg Asp Asp Pro Lys
        115                 120                 125

Trp Asp Val Glu Leu Tyr Glu Arg Tyr Ile Gly Val Val Asp Glu Leu
    130                 135                 140

Gly Gln Tyr Asp Asn Val Val Gly Phe Phe Ala Gly Asn Glu Val Ser
145                 150                 155                 160

Asn Asn Val Ser Asn Thr Glu Ala Ser Ala Phe Val Lys Ala Val Val
                165                 170                 175

Arg Asp Thr Lys Lys His Ile Lys Ser Lys Phe Ser Arg Trp Leu Gly
            180                 185                 190

Val Gly Tyr Ala Ser Asn Asp Asp Val Asp Ile Arg Glu Gln Ile Ala
        195                 200                 205

Asp Tyr Phe Asn Cys Gly Asp Asp Asp Ser Arg Ile Asp Tyr Trp Gly
    210                 215                 220

Tyr Asn Ile Tyr Ser Trp Cys Gly Lys Ser Ser Met Glu Asp Ser Gly
```

```
                    225                 230                 235                 240

Tyr Thr Asp Gln Ala Lys Phe Phe Glu Asn Tyr Ser Val Pro Val Phe
                        245                 250                 255

Phe Ala Glu Tyr Gly Cys Asn Glu Pro Asp Gly Ala Ala Gly Arg Ile
                        260                 265                 270

Phe Asp Glu Thr Thr Ala Leu Tyr Asp Glu Lys Ile Met Thr Glu Val
                        275                 280                 285

Phe Ser Gly Gly Ile Val Tyr Met Tyr Phe Gln Glu Ala Asn Asp Tyr
                        290                 295                 300

Gly Leu Val Lys Ile Asn Lys Asn Asp Asp Ala Val Lys Leu Lys Asp
        305                 310                 315                 320

Phe Ser Ala Leu Gln Ser Lys Val Asn Ala Ala Lys Pro Thr Gly Val
                        325                 330                 335

Glu Glu Asp Ser Tyr Lys Pro Thr Gly Lys Ala Ala Thr Cys Pro Glu
                        340                 345                 350

Gln Ser Lys Asn Trp Lys Ala Asn Ser Val Leu Pro Val Pro Asp
                        355                 360                 365

Ser Asp Leu Cys Asp Cys Met Val Lys Ser Arg Ser Cys Val Pro Ala
                        370                 375                 380

Asp Asn Leu Lys Ala Lys Asp Phe Asn Asp Ile Phe Gly Tyr Ile Cys
        385                 390                 395                 400

Gly Gln Asp Lys Lys Ile Cys Thr Ala Ile Asn Ala Asn Ala Thr Ala
                        405                 410                 415

Gly Ile Tyr Gly Ala Tyr Ser Met Cys Ser Asp Glu Ala Lys Leu Ala
                        420                 425                 430

Tyr Ile Leu Asp Ala Tyr Tyr Val Ser Gln Lys Ser Ala Ala Asp Ala
                        435                 440                 445

Cys Asp Phe Lys Gly Lys Ala Thr Thr Gln Lys Ala Glu Ser Gln Ser
                        450                 455                 460

Ser Cys Ser Ser Ala Leu Ala Ser Ala Ser Lys Ile Asn Glu Glu Val
        465                 470                 475                 480

Ala Thr Ala Thr His Ala Val Ala Ser Glu Ser Thr Gly Gly Thr Asn
                        485                 490                 495

Ser Ser Ser Glu Asp Asp Glu Asn Phe Gly Leu Gln Ala Ala Ser Ile
                        500                 505                 510

Ala Arg Val Phe Ser Leu Gly Asp Phe Ala Val Gly Ala Tyr Met Ala
                        515                 520                 525

Val Ala Gly Ile Val Gly Ala Gly Met Val Leu Leu
        530                 535                 540

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
cggccccgac tcgacaagtc                                                    20

<210> SEQ ID NO 7
<211> LENGTH: 22
<212> TYPE: DNA
<213> ORGANISM: Artificial Sequence
<220> FEATURE:
<223> OTHER INFORMATION: synthetic primer
```

```
<400> SEQUENCE: 7
agcggggcgt gatcctacaa ga                                          22

<210> SEQ ID NO 8
<211> LENGTH: 24
<212> TYPE: DNA
<213> ORGANISM: Artificial Sequence
<220> FEATURE:
<223> OTHER INFORMATION: synthetic primer

<400> SEQUENCE: 8
gttggcggcg tctgtcgtgt agtc                                        24

<210> SEQ ID NO 9
<211> LENGTH: 29
<212> TYPE: DNA
<213> ORGANISM: Artificial Sequence
<220> FEATURE:
<223> OTHER INFORMATION: synthetic primer

<400> SEQUENCE: 9
ttcctgacaa cgaggacatc tcaagctgt                                   29

<210> SEQ ID NO 10
<211> LENGTH: 24
<212> TYPE: DNA
<213> ORGANISM: Artificial Sequence
<220> FEATURE:
<223> OTHER INFORMATION: synthetic primer

<400> SEQUENCE: 10
gtcgtgacgc cctgtctgag catc                                        24

<210> SEQ ID NO 11
<211> LENGTH: 36
<212> TYPE: DNA
<213> ORGANISM: Artificial Sequence
<220> FEATURE:
<223> OTHER INFORMATION: synthetic primer

<400> SEQUENCE: 11
ggtcagtaac atagcaggac tatagtagtg gctcac                           36

<210> SEQ ID NO 12
<211> LENGTH: 2423
<212> TYPE: DNA
<213> ORGANISM: Trichoderma reesei

<400> SEQUENCE: 12
tctgctccag ggcgccgctt gaaaggagca gacctctttt cgcatctttc ttttttgctt    60
ttgcaactta attcatcagt ccttttgac atcgttttt ttgagggcgg ccgcctcgca     120
cagttctggc ctttcagtca ctccttaaga caaacaacca tcatttacat tctatatcgt   180
tccttgacgc cttttgaat ctcttcgtcg cctgaccgag cacgagaagc acacgtccaa    240
tcgctacagc atcaactcaa gaaccgcaag tttcacgact actttcacca gaaccgccaa   300
gatgagcttg tccaagctct ccgtctccct gctcgcactg ctggcagcg ccattgctgg    360 cgatctcccg tccatcacgg ccaaggtgag ccacttttcg tccccagagt ttccctcgtc   420
tcgaacggga gatcagagag ctgtccgagg gatcgaacaa acgatcagca accgtgagat   480
cagcccgcta atcgaccatc tttccgactt gtagggctcc aagttcttct accccaacgg   540
cacccagttc ttcatcaagg gtgttgcgta ccagcaggat gttggccagg ccggaagcac   600
```

```
cgactccagc acctcgacct tcatcgaccc cctctccagc gaggccaact gcaagcgtga    660
cgtccctctg ctgaagcagc tgggcaccaa cgtgatccga acctacgcca tcgaccccaa    720
ggccgaccac tccgcctgca tgaagctgct caacgatgcc ggcatctacg tcttctccga    780
cctgggcgag ccctctctgt ccatcaaccg tgacacccct gcctggaaca ccgagctgtt    840
cgaccgctac aaggccgtcg tcgacgagat gtcccagtac cccaacgtca tcggctactt    900
cgccggtaac gaggtgagca acgccaagaa caacactggc gcctccgcct acgtcaaggc    960
cgctgtccgc gacaccaagg cctacatcaa gtccaagaag taccgctggc agggtgtcgg   1020
ctacgccgcc aacgacgatg tcgacattcg tgccgagatt gccgactact caactgcgg    1080
tgaccaggat gaggctatcg acttctgggg ctacaacatc tactcgtggt gtggccagag   1140
ctccatgcaa aagtccggct acgacgagca gaccaccttc ttctccaact actctgtccc   1200
cgtcttcttc gccgagtacg gctgcaacct gcccagcggc gccgctgccc gtatcttcca   1260
ggagactgct gctctgtact ctgacgagat gaccaaggtc tttagcggtg gtattgtcta   1320
catgtacttt gaggaggaca acgactatgg taggtggtca ttcttatgac tgaacttcag   1380
cagggtcgct aacacgtttc ccaggtctcg tcaaggtcaa caacggcgcc gtctccaagc   1440
tcaaggactt cagcgctctc cagacccagg ttaccaaggc cgaccccaag ggtgttgacg   1500
ccgatgacta caagcccacc aacaagcccg ccagctgccc tgccctgacc gacgactggc   1560
aggccatcaa cagccttccc cccaccgctg atgccagcct ttgcacttgc atgcagagct   1620
ctctgtcctg cgttcacgcc gacgacctcg acaccaagga ctttggcgac atcttcggct   1680
tcatctgcgg caagtccccc gaggtctgcg ctggcatcaa cggtgaccct tccactggtg   1740
tctacggcgc ctacagcatg tgcgaggacg ccgccaagct cgactacgtc cttgacgcct   1800
actaccagtc ccagaagaag gcctccaccg cctgcgactt caacggccag gctcaggtcg   1860
tcagccccaa ggccgcctcc acctgctctg ccgccctggc ctctgccagc gccatcaaca   1920
agcaggccgc cactgccacc gccccgtcg gtgccggttc cacctctggc agcaagggcg   1980
ctgccaccag caccaacgct gctgttgccg gccgccctgt ttcccacctg ctcagcatgg   2040
gcgagatctc cgttgccctg tacatgggtg tcgccatgct ggccggtggt gccatgattg   2100
tcctgtaaag gggatagtcc gagggcctgt ttgttttaaa aatttctgcc gggttttttg   2160
tatgtagatt ggaggttctt ttataggaaa gtgaaataat tcattgtttt tggttcttga   2220
tcattcttct gttttttatt agagcggttc tttttctctt gggaacgaag cttttctttt   2280
cttcgattgc tagaggcatc tttgggttg cgtgtcatgc ggcttgcgct attagaacgg   2340
atggtcttga tagcacttat tgacttttat gattcttgat atttaccccc ttggaccact   2400
ttcatcatag catgtatgaa aac                                           2423
```

FILAMENTOUS FUNGI HAVING AN ALTERED VISCOSITY PHENOTYPE

CROSS REFERENCE TO RELATED APPLICATIONS

The present application is a 371 National Stage application of PCT/US2012/034399, filed on Apr. 20, 2012, which claims priority to U.S. Provisional Application Ser. Nos. 61/478,160, and 61/478,162, both filed on Apr. 22, 2011 and 61/480,602, 61/480,610 and 61/480,629, each filed on Apr. 29, 2011, which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "40010WO_ST25.txt" created on Oct. 11, 2013, which is 28,672 bytes in size.

TECHNICAL FIELD

The present strains and methods relate to genetic mutations in filamentous fungi that give rise to strain variants having altered growth characteristics. Such variants are well-suited for growth in submerged cultures, e.g., for the large-scale production of enzymes and other proteins or metabolites for commercial applications.

BACKGROUND

Filamentous fungi are capable of expressing native and heterologous proteins to high levels, making them well-suited for the large-scale production of enzymes and other proteins for industrial, pharmaceutical, animal health and food and beverage applications. Filamentous fungi are typically grown in mycelial submerged cultures in bioreactors, which are adapted to introduce and distribute oxygen and nutrients into the culture medium (i.e., broth). The morphological characteristics of the mycelium affect the rheological properties of the broth, thereby affecting bioreactor performance.

Generally, the higher the viscosity of the broth, the less uniform the distribution of oxygen and nutrients, and the more energy required to agitate the culture. In some cases, the viscosity of the broth becomes sufficiently high to significantly interfere with the dissolution of oxygen and nutrients, thereby adversely affecting the growth of the fungi. Additionally, the power required to mix and aerate viscous broth can significantly increase the cost of production, and incur higher capital expenditures in terms of motors and power supplies.

SUMMARY

Described are strains and methods relating to filamentous fungi having genetic alterations that give rise to altered viscosity phenotypes.

In one aspect, a variant strain of filamentous fungus derived from a parental strain is provided, the variant strain comprising a genetic alteration that causes cells of the variant strain to produce an altered amount of functional Gas1 protein compared to cells of the parental strain, wherein the cells of the variant strain are produced during aerobic fermentation in submerged culture cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.

In some embodiments, the altered amount of functional Gas1 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.

In some embodiments, the genetic alteration comprises a disruption of the gas1 gene present in the parental strain. In some embodiments, disruption of the gas1 gene is the result of deletion of all or part of the gas1 gene. In some embodiments, disruption of the gas1 gene is the result of deletion of a portion of genomic DNA comprising the gas1 gene. In some embodiments, disruption of the gas1 gene is the result of mutagenesis of the gas1 gene.

In some embodiments, disruption of the gas1 gene is performed using site-specific recombination. In some embodiments, disruption of the gas1 gene is performed in combination with introducing a selectable marker at the genetic locus of the gas1 gene.

In some embodiments, the variant strain does not produce functional Gas1 protein. In some embodiments, the variant strain does not produce Gas1 protein.

In some embodiments, the variant strain further comprises a gene encoding a protein of interest. In some embodiments, the variant strain further comprises a disruption of the sfb3 gene. In some embodiments, the variant strain further comprises a disruption of the seb1gene. In some embodiments, the variant strain further comprises a disruption of the sfb3 and seb1 genes. In some embodiments, the variant strain further comprises a disruption of at least one gene selected from the group consisting of the sfb3 gene, the seb1 gene, the mpg1 gene, the crz1 gene, and the tps2 gene. In some embodiments, the variant strain produces substantially the same amount of, or more, protein per unit amount of biomass as the parental strain.

In some embodiments, the filamentous fungus is a *Pezizomycotina* species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger, Aspergillus fumigatus, Aspergillus itaconicus, Aspergillus oryzae, Aspergillus nidulans, Aspergillus terreus, Aspergillus sojae, Aspergillus japonicus, Scedosporium prolificans, Neurospora crassa, Penicillium funiculosum, Penicillium chrysogenum, Talaromyces (Geosmithia) emersonii, Fusarium venenatum,* and *Chrysosporium lucknowense*. In some embodiments, the filamentous fungus is *Trichoderma reesei*.

In another aspect, a method for producing a variant strain of filamentous fungus cells is provided, comprising: introducing a genetic alteration into a parental strain of filamentous fungal cell, which genetic alteration alters the production of functional Gas1 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

In some embodiments, the genetic alteration reduces or prevents the production of functional Gas1 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

In some embodiments, the genetic alteration comprises disrupting the gas1 gene in a parental filamentous fungal cell using genetic manipulation. In some embodiments, the genetic alteration comprises deleting the gas1 gene in a parental filamentous fungal cell using genetic manipulation. In some embodiments, the genetic alteration is performed using site-specific genetic recombination.

In some embodiments, disruption of the gas1 gene is performed in combination with introducing a selectable marker at the genetic locus of the gas1 gene. In some embodiments, the variant strain produces substantially the same amount of, or more, protein per unit amount of biomass as the parental strain. In some embodiments, disruption of the gas1 gene is performed in combination with disrupting the sfb3 gene. In some embodiments, disruption of the gas1 gene is performed in combination with disrupting at least one gene selected from the group consisting of the sfb3 gene, the seb1 gene, the mpg1 gene, the crz1 gene, and the tps2 gene.

In some embodiments, the variant strain produces substantially the same amount of, or more, protein per unit amount of biomass as the parental strain.

In some embodiments, the filamentous fungus is a *Pezizomycotina* species. In some embodiments, the filamentous fungus is a *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. In some embodiments, the filamentous fungus can include, but is not limited to, *Trichoderma reesei* (previously classified as *Trichoderma longibrachiatum* and *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces* (*Geosmithia*) *emersonii*, *Fusarium venenatum*, and *Chrysosporium lucknowense*. In some embodiments, the filamentous fungus is *Trichoderma reesei*.

In some embodiments, the parental strain further comprises a gene encoding a protein of interest. In some embodiments, the gene encoding the protein of interest is present in the parental strain prior to introducing the genetic alteration that reduces or prevents the production of functional Gas1 protein. In some embodiments the protein of interest within the parental strain is encoded by an endogenous gene or a heterologous gene.

In another aspect, a protein of interest produced by any of the aforementioned variant strains is provided.

In yet another aspect, a filamentous fungus produced by any of the aforementioned methods and having any of the aforementioned properties is provided.

In another aspect, a variant strain of filamentous fungus derived from a parental strain is provided, the variant strain comprising: (a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and (b) a gene encoding a protein of interest, wherein the gene encoding the protein of interest is present in the variant strain prior to the genetic alteration in (a).

In some embodiments, the genetic alteration of the resulting variant strain comprises a disruption of the gas1 gene present in the parental strain. In some embodiments, disruption of the gas1 gene is performed in combination with introducing a selectable marker at the genetic locus of the gas1 gene. In some embodiments, disruption of the gas1 gene is performed in combination with disrupting the sfb3 gene. In some embodiments, disruption of the gas1 gene is performed in combination with disrupting the seb1 gene. In some embodiments, disruption of the gas1 gene is performed in combination with disrupting at least one gene selected from the group consisting of the sfb3 gene, the seb1 gene, the mpg1 gene, the crz1 gene, and the tps2 gene.

These and other aspects and embodiments of present variant strains and methods will be apparent from the description, including the accompanying Figure.

BRIEF DESCRIPTION OF THE DRAWING

FIG. 1 is a map of the gas1 disruption vector, pRATT247-gas1D-pyr2, as described in Example 1.

DETAILED DESCRIPTION

I. Overview

The present strains and methods relate to variant strains of filamentous fungus cells having genetic modifications that affect their morphology and growth characteristics. When the variant cells are grown in submerged culture, they produce a cell broth that has different rheological properties compared to a cell broth comprising cells of the parental strain. Some of these variant strains are well-suited for the large-scale production of enzymes and other commercially important proteins.

II. Definitions

Prior to describing the present strains and methods in detail, the following terms are defined for clarity. Terms not defined should be accorded their ordinary meanings as used in the relevant art.

As used herein, "*Trichoderma reesei*" refers to a filamentous fungus of the phylum Ascomycota, subphylum Pezizomycotina. This organism was previously classified as *Trichoderma longibrachiatum*, or as *Hypocrea jecorina*.

As used herein, the phrase "variant strain of filamentous fungus cells," or similar phrases, refer to strains of filamentous fungus cells that are derived (i.e., obtained from or obtainable from) from a parental (or reference) strain belonging to the *Pezizomycotina*, e.g., by genetic manipulation. In the present description, parental and variant strains can be described as having certain characteristics, such as genetic modifications, expression phenotypes, morphology, and the like; however, the skilled person will appreciate that it is technically the cells of the parental or variant strain that have such characteristics, and "the strains" are referred to for convenience.

As used herein, the term "protein of interest" refers to a polypeptide that is desired to be expressed in a filamentous fungus. Such a protein can be an enzyme, a substrate-binding protein, a surface-active protein, a structural protein, or the like, and can be expressed at high levels, and can be for the purpose of commercialization. The protein of interest can be encoded by an endogenous gene or a heterologous gene relative to the variant strain and/or the parental strain. The protein of interest can be expressed intracellularly or as a secreted protein.

As used herein, the phrase "substantially free of an activity," or similar phrases, means that a specified activity is either undetectable in an admixture or present in an amount that would not interfere with the intended purpose of the admixture.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are deemed "related proteins." Such proteins can be derived from organisms of different genera and/or species, or even different classes of organisms (e.g., bacteria and fungi). Related proteins also encompass homologs determined by primary sequence analysis, determined by secondary or tertiary structure analysis, or determined by immunological cross-reactivity.

As used herein, the term "derivative polypeptide/protein" refers to a protein, which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence, which encodes for the native protein, transformation of that DNA sequence into a suitable host, and expression of the modified DNA sequence to form the derivative protein.

Related (and derivative) proteins include "variant proteins." Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure. The term also refers to nucleotide sequences, as well as amino acid sequences. In some embodiments, analogous sequences are developed such that the replacement amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. Homologs are not necessarily evolutionarily related. Thus, it is intended that the term encompasses the same, similar, or corresponding enzyme(s) (e.g., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity(ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.*, 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, Wis.); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) *CABIOS* 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'S, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (e.g., wild-type) sequence. Sequence identity can be determined using known programs such as BLAST, ALIGN, and CLUSTAL using standard parameters. (See, e.g., Altschul, et al. (1990) *J. Mol. Biol.* 215:403-410; Henikoff et al. (1989) *Proc. Natl. Acad. Sci. USA* 89:10915; Karin et al. (1993) *Proc. Natl. Acad. Sci USA* 90:5873; and Higgins et al. (1988) *Gene* 73:237-244). Software for performing BLAST analyses is publicly available through the National Center for Biotechnology Information. Also, databases can be searched using FASTA (Pearson et al. (1988) *Proc. Natl. Acad. Sci. USA* 85:2444-48). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "wild-type" and "native" are used interchangeably and refer to genes, proteins, or strains found in nature.

As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences.

As used herein, "disruption of a gene" refers broadly to any genetic or chemical manipulation, i.e., mutation, that substantially prevents a cell from producing a function gene product, e.g., a protein, in a host cell. Examples of methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using RNAi, antisense, or any other method that abolishes gene expression.

As used herein, the terms "genetic manipulation" and "genetic alteration" are used interchangeably and refer to the alteration/change of a nucleic acid sequence. The alteration can included but is not limited to a substitution, deletion, insertion or chemical modification of at least one nucleic acid in the nucleic acid sequence.

As used herein, "aerobic fermentation" refers to growth in the presence of oxygen.

As used herein, the term "cell broth" refers collectively to medium and cells in a liquid/submerged culture.

As used herein, the term "cell mass" refers to the cell component (including intact and lysed cells) present in a liquid/submerged culture. Cell mass can be expressed in dry or wet weight.

As used herein, the term "rheology" refers to a branch of physics dealing with the deformation and flow of matter.

As used herein, "viscosity" is a measure of the resistance of a fluid to deformation by mechanical stress, such as shear stress or tensile stress. In the present context, viscosity can also refer to the resistance of a cell broth comprising filamentous fungus cells to mechanical stress, e.g., as provided by a rotor/impeller. Because the viscosity of a cell broth can be difficult to measure directly, indirect measurements of viscosity can be used, such as the dissolved oxygen content of the culture broth at a preselected amount of agitation, the amount of agitation required to maintain a preselected dissolved oxygen content, the amount of power required to agitate a cell broth to maintain a preselected dissolved oxygen content, or even colony morphology on solid medium.

As used herein, an "altered-viscosity" variant strain of filamentous fungus cells refers to a variant strain that produces a cell broth that has a reduced or increased viscosity (i.e., reduced or increased resistance to shear or tensile stress) compared to an equivalent cell broth produced by a parental strain. Generally, comparable cell broths or equivalent cell broths have comparable cell masses. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more. Methods for comparing the viscosity of filamentous fungus cells broth are described herein.

As used herein, a "reduced-viscosity" variant strain of filamentous fungus cells refers to a variant strain that produces a cell broth that has reduced viscosity (i.e., reduced resistance to shear or tensile stress) compared to an equivalent cell broth produced by a parental strain. Preferably, the difference between a variant, altered viscosity strain and a parental strain, with respect to any direct or indirect measure of viscosity, is at least 10%, at least 15%, at least 20%, at least 25%, at least 30%, at least 35%, at least 40%, at least 45%, or even at least 50%, or more.

As used herein, "dissolved oxygen" (DO) refers to the amount of oxygen ($O_2$) present in a liquid medium as measured in vol/vol units. The dissolved oxygen level can be maintained at a high level, e.g., between 170-100% and 20%, between 100-80% and 20%, between 70% and 20%, between 65% and 20%, between 60% and 20%, between 55% and 20%, between 50% and 20%, between 45% and 20%, between 44% and 20%, between 43% and 20%, between 42% and 20%, between 41% and 20%, between 40% and 20%, between 35% and 20%, between 30% and 20%, and between 25% and 20% throughout the fermentation. In particular, the dissolved oxygen can be high at the beginning of the fermentation and to be permitted to fall as the fermentation progresses. The dissolved oxygen level can be controlled by the rate at which the fermentation is agitated, e.g. stirred, and/or by the rate of addition of air or oxygen. The culture can be agitated, e.g., stirred at between 400-700 rpm and the dissolved oxygen level is maintained above 20%, above 25%, above 30%, above 35%, above 40%, above 45%, above 50% and above 55% or more by altering the air or oxygen flow rate and impeller speed.

As used herein, a "primarily genetic determinant" refers to a gene, or genetic manipulation thereof, that is necessary and sufficient to confer a specified phenotype in the absence of other genes, or genetic manipulations, thereof. However, that a particular gene is necessary and sufficient to confer a specified phenotype does not exclude the possibility that additional effects to the phenotype can be achieved by further genetic manipulations.

As used herein, a "functional polypeptide/protein" is a protein that possesses an activity, such as an enzymatic activity, a binding activity, a surface-active property, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, variant cells "maintain or retain a high level of protein expression and/or secretion" compared to a parental strain if the difference in protein expression between the variant strain and a parental strain is less than about 20%, less than about 15%, less than about 10%, less than about 7%, less than about 5%, or even less than about 3%.

As used herein, host cells have been "modified to prevent the production of a specified protein" if they have been genetically or chemically altered to prevent the production of a functional protein/polypeptide that exhibits an activity characteristic of the wild-type protein, particularly an activity that promotes elongation of hyphae or otherwise increases the viscosity of a filamentous fungus in liquid culture. Such modifications include, but are not limited to, deletion or disruption of the gene encoding the protein, modification of the gene such that the encoded polypeptide lacks the aforementioned activity, modification of the gene to affect post-translational processing or stability, and combinations, thereof.

As used herein, a "protein of interest" is a protein that is desired to be produced in a submerged culture of filamentous fungus cells. Generally, proteins of interest are commercially important for industrial, pharmaceutical, animal health, and food and beverage use, making them desirable to produce in large quantities. Proteins of interest are to be distinguished from the myriad other proteins expressed by the filamentous fungus cells, which are generally not of interest as products and are mainly considered background protein contaminants.

As used herein, a variant strain produces "substantially the same amount" of protein per unit amount of biomass as a parental strain if the amount of protein produced by the variant strain is no more than 20% reduced, no more than 15% reduced, no more than 10% reduced, an even no more than 5% reduced compared to the amount of protein produced by the parental strain, wherein the amount of protein is normalized to the total amount of biomass of cells from which protein production is measured, wherein biomass can be expressed in terms of either wet (e.g., of cell pellet) or dry weight.

As used herein, a variant strain produces "substantially more protein per unit amount of biomass" than a parental strain if the amount of protein produced by the variant strain is at least 5% increased, at least 10% increased, at least 15% increased, or more, compared to the parental strain, wherein the amount of protein is normalized to the total amount of biomass of cells from which protein production is measured, wherein biomass can be expressed in terms of either wet (e.g., of cell pellet) or dry weight.

As used herein, "fluorochromes" are fluorescent dyes. Preferred fluorochromes bind to cellulose and/or chitin in the cell walls of fungi.

As used herein, the singular articles "a," "an," and "the" encompass the plural referents unless the context clearly dictates otherwise. All references cited herein are hereby incorporated by reference in their entirety. The following abbreviations/acronyms have the following meanings unless otherwise specified:

CFU colony forming units
EC enzyme commission
kDa kiloDalton
kb kilobase
MW molecular weight
w/v weight/volume
w/w weight/weight
v/v volume/volume
wt % weight percent
° C. degrees Centigrade
$H_2O$ water
$H_2O_2$ hydrogen peroxide
$dH_2O$ or DI deionized water
$dIH_2O$ deionized water, Milli-Q filtration
DO dissolved oxygen
g or gm gram
μg microgram
mg milligram
kg kilogram
lb pound
μL and μl microliter
mL and ml milliliter
mm millimeter
μm micrometer
mol mole
mmol millimole
M molar
mM millimolar
μM micromolar
nm nanometer
U unit
ppm parts per million
sec and " second
min and ' minute
hr and h hour
EtOH ethanol
eq. equivalent
N normal
PCR polymerase chain reaction
DNA deoxyribonucleic acid
FOA fluoroorotic acid
UV ultraviolet
$A_{540}$ absorbance measured at a wavelength of 540 nm
CMC carboxymethyl cellulose
rpm revolutions per minute
Δ relating to a deletion
CER $CO_2$ evolution rate
bp base pairs

III. Filamentous Fungal Strain with Altered Gas1 Protein Production

In one aspect, a variant strain of filamentous fungus derived from a parental strain is provided, the variant strain comprising a genetic alteration that causes cells of the variant strain to produce an altered amount of functional Gas1 protein compared to cells of the parental strain. The cells of the variant strain subsequently produce, during aerobic fermentation in submerged culture, a cell broth that requires an altered amount of agitation to maintain a preselected dissolved oxygen content, or a cell mass that maintains an altered dissolved oxygen content at a preselected amount of agitation, compared to the cells of the parental strain.

In some cases, the genetic alteration causes cells of the variant strain to produce a reduced amount of functional Gas1 protein compared to cells of the parental strain, and the resulting cell broth requires reduced agitation to maintain a preselected dissolved oxygen content, or maintains a higher dissolved oxygen content at a preselected amount of agitation, compared to the cells of the parental strain. In such cases, it is believed that the cell mass of the variant strain exhibits reduced viscosity compared to the cell mass of the parental strain, which accounts for the observations relating to dissolved oxygen content and agitation as described in the Examples.

The reduction in the amount of functional Gas1 protein can result from disruption of the gas1 gene present in the parental strain. Because disruption of the gas1 gene is a primary genetic determinant for conferring a reduced viscosity phenotype to the variant strain, such variant strains need only comprise a disrupted gas1 gene, while all other genes can remain intact. In some cases, the variant strains can optionally include additional genetic alterations compared to the parental stain from which they are derived. Such additional genetic alterations are not necessary to confer a reduction in viscosity but can further reduce viscosity or confer other advantages for the variant strain.

Disruption of the gas1 gene can be performed using any suitable methods that substantially prevent expression of a function gas1 gene product, i.e., the Gas1 protein. Exemplary methods of disruption as are known to one of skill in the art include but are not limited to: Complete or partial deletion of the gas1 gene, including complete or partial deletion of, e.g., the Gas1-coding sequence, the promoter, the terminator, an enhancer, or another regulatory element; and complete or partial deletion of a portion of the chromosome that includes any portion of the gas1 gene. Particular methods of disrupting the gas1 gene include making nucleotide substitutions or insertions in any portion of the gas1 gene, e.g., the Gas1-coding sequence, the promoter, the terminator, an enhancer, or another regulatory element. Preferably, deletions, insertions, and/or substitutions (collectively referred to as mutations) are made by genetic manipulation using sequence-specific molecular biology techniques, as opposed to by chemical mutagenesis, which is generally not targeted to specific nucleic acid sequences. Nonetheless, chemical mutagenesis can be used to disrupt the gas1 gene.

Mutations in the gas1 gene can reduce the efficiency of the gas1 promoter, reduce the efficiency of a gas1 enhancer, interfere with the splicing or editing of the gas1 mRNA, interfere with the translation of the gas1 mRNA, introduce a stop codon into the Gas1-coding sequence to prevent the translation of full-length Gas1 protein, change the coding sequence of the Gas1 protein to produce a less active or inactive protein or reduce Gas1 interaction with other nuclear protein components, change the coding sequence of the Gas1 protein to produce a less stable protein or target the protein for destruction, cause the Gas1 protein to misfold or be incorrectly modified (e.g., by glycosylation), or interfere with cellular trafficking of the Gas1 protein.

In one embodiment, these and other genetic manipulations is to reduce or prevent the expression of a functional Gas1 protein, or reduce or prevent the normal biological activity of the Gas1 protein, thereby producing a morphology change that results in a reduced viscosity phenotype.

In other cases, the genetic alteration increases or restores the expression of a functional Gas1 protein, or increases the normal biological activity of the Gas1 protein, thereby producing a morphology change that results in an increased or restored viscosity phenotype. Exemplary genetic alterations that increase or restore Gas1 function are those that introduce addition copies of the gas1 gene into a cell, increase the efficiency of the gas1 promoter, enhancer, or other control element, increase the translation of the mRNA encoding the Gas1 protein, increase the stability of mRNA encoding the Gas1 protein, introduce changes in the gas1 gene that increase the activity or stability of the Gas1 protein, introduce changes in the gas1 gene that modulate the interaction with other proteins or nucleic acids and the like. Other genetic alterations that increase or restore Gas1 function are those that reverse the effect of genetic alterations, which reduce or prevent the expression of a functional Gas1 protein.

Filamentous fungus cells for manipulation and use as described are generally from the phylum Ascomycota, subphylum *Pezizomycotina*, particularly fungi that have a vegetative hyphae state and include a homolog of the gas1 gene. Such organisms include filamentous fungus cells used for the production of commercially important industrial and pharmaceutical proteins, including, but are not limited to *Trichoderma* spp., *Aspergillus* spp., *Fusarium* spp., *Scedosporium* spp., *Penicillium* spp., *Chrysosporium* spp., *Cephalosporium* spp., *Talaromyces* spp., *Geosmithia* spp., and *Neurospora* spp. Particular organisms include, but are not limited to, *Trichoderma reesei* (previously classified as *Trichoderma longibrachiatum* or *Hypocrea jecorina*), *Aspergillus niger*, *Aspergillus fumigatus*, *Aspergillus itaconicus*, *Aspergillus oryzae*, *Aspergillus nidulans*, *Aspergillus terreus*, *Aspergillus sojae*, *Aspergillus japonicus*, *Scedosporium prolificans*, *Neurospora crassa*, *Penicillium funiculosum*, *Penicillium chrysogenum*, *Talaromyces* (*Geosmithia*) *emersonii*, *Fusarium venenatum*, and *Chrysosporium lucknowense*.

The Gel/Gas/Phr family of fungal β(1,3)-glucanosyltransferases plays an important role in cell wall biogenesis by processing the main component β(1,3)-glucan (Popolo et al., 2008). Gas1 (PID 22914) encodes a beta-1,3-glucanosyltransferase that is a GPI (and/or glucan)-anchored protein capable of breaking and joining beta-1,3-glucans. There are multiple paralogs in many fungal genomes including *T. reesei*, which has five. Separate studies have shown that mutation of the gas1 gene (or the gel1 gene as it is known in *Aspergillus fumigatus*) affects fungal cell wall structure, and can lead to morphological changes as well as hypersensitivity to Calcofluor White, Congo Red and sodium dodecyl sulfate (Schirawski, J. et al. 2005, Mouyna, I. et al. 2005). The present disclosure provides experimental evidence of the association of Gas1 with altered morphology.

Not wishing to be bound to a theory, it is believed that the alteration of gas1 expression and/or activity in filamentous fungi interferes with cell wall synthesis, thereby producing a more compact cellular morphology characterized by shorter hyphae and a more yeast-like appearance.

The predicted amino acid sequence of the *Trichoderma reesei* Gas1 (jgi|Trire2|22914) protein is shown, below, as SEQ ID NO: 1:

MSLSKLSVSLLALAGSAIAGDLPSITAKGSKFFYPNGTQFFIKGVAYQQDVGQAGSTDSS

TSTFIDPLSSEANCKRDVPLLKQLGTNVIRTYAIDPKADHSACMKLLNDAGIYVFSDLGE

PSLSINRDTPAWNTELFDRYKAVVDEMSQYPNVIGYFAGNEVSNAKNNTGASAYVKAA

VRDTKAYIKSKKYRWQGVGYAANDDVDIRAEIADYFNCGDQDEAIDFWGYNIYSWCG

QSSMQKSGYDEQTTFFSNYSVPVFFAEYGCNLPSGAAARIFQETAALYSDEMTKVFSGGI

VYMYFEEDNDYGLVKVNNGAVSKLKDFSALQTQVTKADPKGVDADDYKPTNKPASCP

ALTDDWQAINSLPPTPDASLCTCMQSSLSCVHADDLDTKDFGDIFGFICGKSPEVCAGIN

GDPSTGVYGAYSMCEDAAKLDYVLDAYYQSQKKASTACDFNGQAQVVSPKAASTCSA

ALASASAINKQAATATAPVGAGSTSGSKGAATSTNAAVAGRPVSHLLSMGEISVALYM

GVAMLAGGAMIVL

The amino acid sequence of the *Fusarium oxysporum* Gas1 protein is shown, below, as SEQ ID NO: 2:

MKFSAAIVAAAATAASAKLEPITMKGSKLFYSNGTQFFMKGVAYQQDTAAAGETNDKT

TKYIDPLADEEACKRDIPLLKQLGTNIIRTYAINPKADHKACMKLLDAGIYVISDLSEPSV

SINRDDPKWDVELYERYIGVVDELGQYDNVVGFFAGNEVSNNVSNTQASAFVKAAVRD

TKKHIKSKFSRWLGVGYASNDDVDIREQIADYFNCGDDDSRIDYWGYNIYSWCGKSSM

QDSGYSDQAKFFEDYSVPVFFAEYGCNEPDGAAGRIFDETTALYEEKVMTDVFSGGIVY

MYFQEANDYGLVKISKNGDAVKQKDFAQLQKKANAAKPSGVEEDSYKPTGKAATCPE

QSKNWKANSVLPPVPDSDLCDCMVKSRSCVPADNLKAKDFNDIFGYICGQDKKICTAIN

ANATAGIYGAYSMCSNEAKLAYILDAYYTSQKSAADACDFKGKATTQKAESQDSCKSA

LASASKINEEVATATHAVASSSTGGSNSSSEDDENFGLQAASIARVFSLGDFAVGAYMA

VAGVVGAGMVLL

The amino acid sequence of the *Aspergillus niger* CBS 513.88 Gel3 (Gas1) protein is shown, below, as SEQ ID NO: 3:

MKLSLAVGAALMGSALAVDIDPIVIKGSKFFYSSNNTQFYIRGVAYQDDYTGNSSSGYT

DPLANPTLCKRDIPILQELNTNVIRVYAIDPTKDHTTCMNLLAAAGIYVISDLSDPTQSIDR

SDPTWETSLYTRYTNVIDELIQYNNTLAFFAGNEVSNDVATTDASAFVKAAVRDMKAYI

KSQGYRSIGVGYATNDDSDIRVNMADYFNCGSEDESIDFWGYNIYSWCGDSSYTKSGY

DERTEEFRNYSVPVFFSEYGCNTVQPRKFTDIKALFGDQMNDVWSGGIVYMYFQTDND

YGLVSAIDSTSVSKLADFTYYSSQIASATPSGTNKASYTPTNTALQSCPAVTSKSWLATSS

PLPPTPNQELCTCMDNASGCVVKDSVSSSDYDDLFSTVCGFTSCDGIFHNGTTGTYGAY

SMCGAKQQLNFVLDKYWKEQGKKADACGFDGSATTTATVKATGTCSALMKEAGTAG

TGTVTSKPTGTAAGSSSASGTGGVSAVGSGSAIISIGAWQVGAYVVTGVVAGLGMVLL

The amino acid sequence of the *Aspergillus oryzae* RIB40 Gel3 protein is shown below as SEQ ID NO:4

MKLSSIVAGASLFASSVIAADLDPIIIKGSKFFYKSNDTQFYIRGVAYQQEYSGPDSSANSF

KDPLADADACKRDVPYLEKLGTNTIRVYAIDPKSDHKECMSLLSDAGIYVIADLSSPGDS

INRNEPKWDNDLYNRYVTVVDELSQYSNVIGFFAGNEVSNSENTTSASAFVKAAVRDT

-continued

```
KQYIKAKNYRSMGVGYATSDDSSIRKNMANYFNCNGADDSIDFWGYNVYSWCGDSNY

EKSGYASRTEEFKDYTVPVFFAEYGCNAVQPRKFTEVQALYGDKMADVWSGGIVYMY

FQEENNYGLVSVDGNKVSTKADFSYLSKELASATPSGTKKGDYQPTNTALQSCPTVDD

KWLATSSPLPPSPNQDLCSCMEESLSCALKDKVSGEQLDKLFGTVCGYDVCDGITTNAT

TGKYGAYSVCTPQQQLSYAINLYYQNQKAKGNGDKACDFNGAATTQSSKSGGSACSAL

LKEAGTSGTGTVTSSPTGTAGSGASDGAAASSSGSAGGLVAPSSVNVGIFQLGAYVVTA

MVAGAGMIVL
```

The amino acid sequence of the *Gibberella moniliformis* Gas1 protein is shown below as SEQ ID NO:5:

```
MKFSAAIVAAAATAASAKLEPITMKGSKLFYSNGTQFFMKGVAYQQDTAAAGQTNTKE

TKYIDPLADEDACKRDIPLLKQLGTNIIRTYAIDPTADHKACMKLLDDAGIYVISDLSEPS

VSINRDDPKWDVELYERYIGVVDELGQYDNVVGFFAGNEVSNNVSNTEASAFVKAVVR

DTKKHIKSKFSRWLGVGYASNDDVDIREQIADYFNCGDDDSRIDYWGYNIYSWCGKSS

MEDSGYTDQAKFFENYSVPVFFAEYGCNEPDGAAGRIFDETTALYDEKIMTEVFSGGIV

YMYFQEANDYGLVKINKNDDAVKLKDFSALQSKVNAAKPTGVEEDSYKPTGKAATCP

EQSKNWKANSVLPPVPDSDLCDCMVKSRSCVPADNLKAKDFNDIFGYICGQDKKICTAI

NANATAGIYGAYSMCSDEAKLAYILDAYYVSQKSAADACDFKGKATTQKAESQSSCSS

ALASASKINEEVATATHAVASESTGGTNSSSEDDENFGLQAASIARVFSLGDFAVGAYM

AVAGIVGAGMVLL
```

In some embodiments of the present compositions and methods, the amino acid sequence of the Gas1 protein that is altered in production levels has a specified degree of overall amino acid sequence identity to the amino acid sequence of SEQ ID NOs: 1, 2, 3, 4, or 5, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, 3, 4, or 5. The nucleotide sequences encoding each amino acid sequence can be identified from a BLAST search for each corresponding protein as is know to one skilled in the art.

In some embodiments of the present compositions and methods, the gas1 gene that is disrupted encodes a Gas1 protein that has a specified degree of overall amino acid sequence identity to the amino acid sequence of SEQ ID NOs: 1, 2, 3, 4, or 5, e.g., at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NOs: 1, 2, 3, 4, or 5.

The amino acid sequence information provided herein readily allows the skilled person to identify a Gas1 protein, and the nucleic acid sequence encoding a Gas1 protein, in any filamentous fungi, and to make appropriate disruptions in the gas1 gene to affect the production of the Gas1 protein. The polynucleotide sequences encoding SEQ ID NOs: 1, 2 and 3 can be found in the GenBank or JGI databases, as are known to one of skill in the art.

In another aspect, a method for altering the morphology of filamentous fungus cells is provided. The variant filamentous fungus cells exhibit altered growth morphology on solid medium and produce cell broth having different viscosities when grown in submerged culture compared to parental cell growth and cell broth viscosities.

In some cases, the method comprises disrupting the gas1 gene in a parental strain using suitable genetic methods, wherein during aerobic fermentation the disrupted gas1 variant strain produces during aerobic fermentation in submerged culture a cell broth that requires reduced agitation to maintain a preselected dissolved oxygen content, or maintains an increased dissolved oxygen content at a preselected amount of agitation, compared to the cells of the parental strain. Such methods can be used to disrupt the gas1 gene in any manner described above and elsewhere as are known to one of skill in the art. Preferably, disruption of the gas1 gene is performed by genetic manipulation using sequence-specific molecular biology techniques, as opposed to chemical mutagenesis, which is generally not targeted to specific nucleic acid sequences. However, chemical mutagenesis can also be used to achieve satisfactory results.

In some embodiments, the parental strain into which the reduced viscosity phenotype is introduced creating a reduced viscosity strain already comprises a gene of interest intended to be expressed at high levels. In this manner, the present methods obviate the need to introduce a gene of interest into a pre-existing reduced viscosity strain for production. Thus, the present methods can be used to produce a reduced viscosity variant strain of filamentous fungus cells from a parental strain already comprising a gene of interest.

VI. Utility

The use of reduced viscosity strains of filamentous fungi is known to improve the distribution of oxygen and nutrients in a submerged culture, reduce the amount of energy required to agitate a submerged culture, and increase the cell mass present in the culture, leading to increased protein production. Moreover, the present variant strains of filamentous fungus offer significant advantages over previously-described reduced viscosity strains.

First, the present variant strains can have a fully defined genome, making them well-suited for subsequent genetic manipulation, complementation, mating, and the like. Second, the present strains are not adversely affected in protein production, for example, by the manipulation(s) that resulted in the attendant viscosity alteration. Third, reduced viscosity strains can be produced from essentially any parental strain, including parental strains that already produce a protein intended for high level expression (i.e., a protein of interest), already encoding a selectable marker, or already including other features that are desirable in a production host. Thus, the present strain and methods eliminate the need to transfer a gene encoding a protein of interest into a preexisting reduced viscosity production strain.

The present strains and methods find use in the production of commercially important protein in submerged cultures of filamentous fungi. Commercially important proteins include, for example, cellulases, xylanases, pectinases, lyases, proteases, kinases, amylases, pullulanases, lipases, esterases, perhydrolases, transferases, laccases, catalases, oxidases, reductases, chlorophyllases, hydrophobin, chymosin, carbonic anhydrase, hymidylate synthase, dihydrofolate reductase, tyrosine kinases, multi-drug resistance proteins (e.g., ABC P-gp proteins), CAD (carbamyl-P synthase, aspartate transcarbamylase, dihydroorotase), topoisomerases, ribonucleotide reductase, and antibodies and other enzymes and non-enzyme proteins capable of being expressed in filamentous fungi. Such proteins can be suitable for industrial, pharmaceutical, animal health and food and beverage use.

The following numbered paragraphs further describe various aspects and embodiments of the present compositions and methods. The subject matter of each of the numbered paragraphs can be used alone or in combination with the subject matter of any other numbered paragraph, as indicated.

1. In one aspect, a variant strain of filamentous fungus derived from a parental strain is provided, the variant strain comprising a genetic alteration that causes cells of the variant strain to produce an altered amount of functional Gas1 protein compared to cells of the parental strain, wherein the cells of the variant strain produce during aerobic fermentation in submerged culture a cell broth that (i) requires an altered amount of agitation to maintain a preselected dissolved oxygen content compared to the cells of the parental strain, and/or (ii) maintains an altered dissolved oxygen content at a preselected amount of agitation, compared to the cells of the parental strain.
2. In some embodiments of the variant strain of paragraph 1, the altered amount of functional Gas1 protein is a reduced amount, and the variant strain produces during aerobic fermentation in submerged culture a cell broth that (i) requires reduced agitation to maintain a preselected dissolved oxygen content compared to the cells of the parental strain, and/or (ii) maintains an increased dissolved oxygen content at a preselected amount of agitation, compared to the cells of the parental strain.
3. In some embodiments of the variant strain of paragraphs 1 or 2, the genetic alteration comprises a disruption of the gas1 gene present in the parental strain.
4. In some embodiments of the variant strain of paragraph 3, disruption of the gas1 gene is the result of deletion of all or part of the gas1 gene.
5. In some embodiments of the variant strain of paragraph 3, disruption of the gas1 gene is the result of deletion of a portion of genomic DNA comprising the gas1 gene.
6. In some embodiments of the variant strain of paragraph 3, disruption of the gas1 gene is the result of mutagenesis of the gas1 gene.
7. In some embodiments of the variant strain of any of paragraphs 3-6, disruption of the gas1 gene is performed using site-specific recombination.
8. In some embodiments of the variant strain of any of paragraphs 3-7, disruption of the gas1 gene is performed in combination with introducing a selectable marker at the genetic locus of the gas1 gene.
9. In some embodiments of the variant strain of any of paragraphs 1-8, the variant strain does not produce functional Gas1 protein.
10. In some embodiments of the variant strain of any of paragraphs 1-8, the variant strain does not produce Gas1 protein.
11. In some embodiments of the variant strain of any of paragraphs 1-10, the variant strain further comprises a gene encoding a protein of interest.
12. In some embodiments of the variant strain of any of paragraphs 1-11, further comprising a disruption of the sfb3 gene.
13. In some embodiments of the variant strain of any of paragraphs 1-12, further comprising a disruption of at least one gene selected from the group consisting of the sfb3 gene, the seb1 gene, the mpg1 gene, the crz1 gene, and the tps2.
14. In some embodiments of the variant strain of any of paragraphs 1-13, the variant strain produces substantially the same amount of, or more, protein per unit amount of biomass as the parental strain.
15. In some embodiments of the variant strain of any of paragraphs 1-14, the filamentous fungus is a *Pezizomycotina* species.
16. In some embodiments of the variant strain of any of paragraphs 1-15, the filamentous fungus is a *Trichoderma* spp.
17. In some embodiments of the variant strain of any of paragraphs 1-16, the filamentous fungus is *Trichoderma reesei*.
18. In another aspect, a method for producing a variant strain of filamentous fungus cells is provided, comprising: introducing a genetic alteration into a parental strain of filamentous fungal cell, which genetic alteration alters the production of functional Gas1 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.
19. In some embodiments of the method of paragraph 18, the genetic alteration reduces or prevents the production of functional Gas1 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.
20. In some embodiments of the method of paragraph 18 or 19, the genetic alteration comprises disrupting the gas1 gene in a parental filamentous fungal cell using genetic manipulation.
21. In some embodiments of the method of any of paragraphs 18-20, the genetic alteration comprises deleting the gas1 gene in a parental filamentous fungal cell using genetic manipulation.
22. In some embodiments of the method of any of paragraphs 18-21, the genetic alteration is performed using site-specific genetic recombination.
23. In some embodiments of the method of any of paragraphs 18-22, disruption of the gas1 gene is performed in combination with introducing a selectable marker at the genetic locus of the gas1 gene.
24. In some embodiments of the method of any of paragraphs 18-23, disruption of the gas1 gene is performed in combination with disrupting the sfb3 gene.
25. In some embodiments of the method of any of paragraphs 18-24, disruption of the gas1 gene is performed in combination with disruption of at least one gene selected from the group consisting of the sbf1 gene, the seb1 gene, the mpg1 gene, the crz1 gene, and the tps2 gene.
26. In some embodiments of the method of any of paragraphs 18-25, the variant strain produces substantially the same amount of, or more, protein per unit amount of biomass as the parental strain.
27. In some embodiments of the method of any of paragraphs 18-26, the filamentous fungus is a Pezizomycotina species.
28. In some embodiments of the method of any of paragraphs 18-27, the filamentous fungus is a Trichoderma spp.
29. In some embodiments of the method of any of paragraphs 18-28, the filamentous fungus is Trichoderma reesei.
30. In some embodiments of the method of any of paragraphs 18-29, the parental strain further comprises a gene encoding a protein of interest.
31. In some embodiments of the method of paragraph 30, the gene encoding the protein of interest is present in the parental strain prior to introducing the genetic alteration that reduces or prevents the production of functional Gas1 protein.
32. In another aspect, a protein of interest produced by the variant strain of paragraph 11 is provided.
33. In another aspect, a variant strain of filamentous fungus produced by the method of any of paragraphs 18-31 is provided.
34. In another aspect, a variant strain of filamentous fungus derived from a parental strain is provided, the variant strain comprising:
(a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, and
(b) a gene encoding a protein of interest, wherein the gene encoding the protein of interest is present in the variant strain prior to the genetic alteration in (a).
35. In some embodiments of the variant strain of paragraph 34, the genetic alteration comprises a disruption of the gas1 gene present in the parental strain.
36. In some embodiments of the variant strain of paragraph 35, disruption of the gas1 gene is performed in combination with introducing a selectable marker at the genetic locus of the gas1 gene.
37. In some embodiments of the variant strain of paragraph 35 or 36, disruption of the gas1 gene is performed in combination with disrupting at least one gene selected from the group consisting of the sfb3 gene, the seb1 gene, the mpg1 gene, the crz1 gene, and the tps2 gene.
38. In some embodiments of the variant strain of any of paragraphs 35-37, disruption of the gas1 gene is performed in combination with disrupting the seb1 gene.

These and other aspects and embodiments of the present strains and methods will be apparent to the skilled person in view of the present description. The following examples are intended to further illustrate, but not limit, the strains and methods.

EXAMPLES

Example 1

Deletion of the gas1 Gene from T. reesei Mutant Morph 77B7

A Trichoderma reesei Morph strain was deleted for four major cellulase genes, including cbhI, cbhII, egII, and egIV, which makes it particular suitable for expressing other proteins in the absence of or in reduced cellulase background. See, WO 05/001036.

A. TrGA Producing Strain Morph 77B7

The Morph strain, described above, was previously transformed with a native Trichoderma glucoamylase gene (TrGA) under control of the CBH1 promoter, using amdS as a marker. A transformant containing two tandem copies of glucoamylase (TrGA 29-9) was subsequently isolated, and random chemical mutagenesis was used to produce a mutant (77B7). A spontaneous pyr2 mutant derivative was subsequently isolated by 5-fluoro-orotic acid (FOA) selection.

B. Generation of a gas1 Disruption Cassette

The Trichoderma reesei gas1 (PID 22914) was deleted from mutant Morph 77B7. The gas1 disruption cassette plasmid pRATT247 (FIG. 1) was prepared using standard molecular biology procedures. This plasmid included a DNA sequence having a 2.6 Kb region homologous to the DNA sequence 55 bp upstream of the 5' untranslated region and contiguous upstream sequences (Left Flank). Also included within the plasmid was a DNA sequence having a 2.7 Kb region homologous to the DNA sequence spanning part of the second exon of the gas1 gene and contiguous downstream sequences (Right Flank). These sequences were designed to target the gas1 gene and replace the regions of the genome between the Left and Right Flanks, region 182010 to 182428 on Scaffold 18 (JGI Trichoderma reesei genomic database v2) with the intervening cassette sequences. These intervening sequences included a pyr2 selection marker from Trichoderma atroviride intended to minimize homology to the endogenous T. reesei pyr2 in the genome of the strain to be transformed. Immediately upstream of the pyr2 selection marker was a directly repeated duplication of the 3' end of the marker, which facilitated the subsequent loss of the marker and isolation of useful pyr2 mutant derivatives of the transformants/disruptants. This gas1 disruption cassette was amplified by PCR using primers RPG111 and RPG381. Multiple PCR reactions were pooled and cleaned using standard molecular biology procedures for use in the subsequent steps.

The nucleic acid sequence of the gas1 gene was obtained from the JGI data base: Protein ID: 22914, Name: estExt_fgenesh1_pm.C_180019, available at http://genome.jgi-psf.org/cgi-bin/dispGeneModel?db=Trire2&id=22914, (The Genome Portal of the Department of Energy Joint Genome Institute I. V. Grigoriev, H. Nordberg, I. Shabalov, A. Aerts, M. Cantor, D. Goodstein, A. Kuo, S. Minovitsky, R. Nikitin, R. A. Ohm, R. Otillar, A. Poliakov, I. Ratnere, R. Riley, T. Smirnova, D. Rokhsar, and I. Dubchak. Nucleic Acids Res 2011 0: gkr947v1-gkr947) as disclosed below. The untranslated region is italicized and flanked 5' and 3' by upstream or downstream sequence, coding regions are in bold and introns are in lower case (SEQ ID NO: 12):

TCTGCTCCAGGGCGCCGCTTGAAAGGAGCAGACCTCTTTTCGCATCTTTCTTTTTTGCTTTTGCAAC

TTAATTCATCAGTCCTTTTTGACATCGTTTTTTTTGAGGGCGGCCGCCTCGCACAGTTCTGGCCTTT

CAGTCACTCCTTAAGACAAACAACCATCATTTACATTCTATATCGTTCCTTGACGCCTTTTTGAATC

*TCTTCGTCGCCTGACCGAGCACGAGAAGCACACGTCCAATCGCTACAGCATCAACTCAAGAACCGCA*

*AGTTTCACGACTACTTTCACCAGAACCGCCAAG*ATGAGCTTGTCCAAGCTCTCCGTCTCCCTGCTCG

CACTGGCTGGCAGCGCCATTGCTGGCGATCTCCCGTCCATCACGGCCAAGgtgagccactttcgtc cccagagtttccctcgtctcgaacgggagatcagagagctgtccgagggatcgaacaaacgatcagc aaccgtgagatcagcccgctaatcgaccatctttccgacttgtagGGCTCCAAGTTCTTCTACCCCA

ACGGCACCCAGTTCTTCATCAAGGGTGTTGCGTACCAGCAGGATGTTGGCCAGGCCGGAAGCACCGA

CTCCAGCACCTCGACCTTCATCGACCCCCTCTCCAGCGAGGCCAACTGCAAGCGTGACGTCCCTCTG

CTGAAGCAGCTGGGCACCAACGTGATCCGAACCTACGCCATCGACCCCAAGGCCGACCACTCCGCCT

GCATGAAGCTGCTCAACGATGCCGGCATCTACGTCTTCTCCGACCTGGGCGAGCCCTCTCTGTCCAT

CAACCGTGACACCCCTGCCTGGAACACCGAGCTGTTCGACCGCTACAAGGCCGTCGTCGACGAGATG

TCCCAGTACCCCAACGTCATCGGCTACTTCGCCGGTAACGAGGTGAGCAACGCCAAGAACAACACTG

GCGCCTCCGCCTACGTCAAGGCCGCTGTCCGCGACACCAAGGCCTACATCAAGTCCAAGAAGTACCG

CTGGCAGGGTGTCGGCTACGCCGCCAACGACGATGTCGACATTCGTGCCGAGATTGCCGACTACTTC

AACTGCGGTGACCAGGATGAGGCTATCGACTTCTGGGGCTACAACATCTACTCGTGGTGTGGCCAGA

GCTCCATGCAAAAGTCCGGCTACGACGAGCAGACCACCTTCTTCTCCAACTACTCTGTCCCCGTCTT

CTTCGCCGAGTACGGCTGCAACCTGCCCAGCGGCGCCGCTGCCCGTATCTTCCAGGAGACTGCTGCT

CTGTACTCTGACGAGATGACCAAGGTCTTTAGCGGTGGTATTGTCTACATGTACTTTGAGGAGGACA

ACGACTATGgtaggtggtcattcttatgactgaacttcagcagggtcgctaacacgtttcccagGTC

TCGTCAAGGTCAACAACGGCGCCGTCTCCAAGCTCAAGGACTTCAGCGCTCTCCAGACCCAGGTTAC

CAAGGCCGACCCCAAGGGTGTTGACGCCGATGACTACAAGCCCACCAACAAGCCCGCCAGCTGCCCT

GCCCTGACCGACGACTGGCAGGCCATCAACAGCCTTCCCCCCACCCCTGATGCCAGCCTTTGCACTT

GCATGCAGAGCTCTCTGTCCTGCGTTCACGCCGACGACCTCGACACCAAGGACTTTGGCGACATCTT

CGGCTTCATCTGCGGCAAGTCCCCCGAGGTCTGCGCTGGCATCAACGGTGACCCTTCCACTGGTGTC

TACGGCGCCTACAGCATGTGCGAGGACGCCGCCAAGCTCGACTACGTCCTTGACGCCTACTACCAGT

CCCAGAAGAAGGCCTCCACCGCCTGCGACTTCAACGGCCAGGCTCAGGTCGTCAGCCCCAAGGCCGC

CTCCACCTGCTCTGCCGCCCTGGCCTCTGCCAGCGCCATCAACAAGCAGGCCGCCACTGCCACCGCC

CCCGTCGGTGCCGGTTCCACCTCTGGCAGCAAGGGCGCTGCCACCAGCACCAACGCTGCTGTTGCCG

GCCGCCCTGTTTCCCACCTGCTCAGCATGGGCGAGATCTCCGTTGCCCTGTACATGGGTGTCGCCAT

GCTGGCCGGTGGTGCCATGATTGTCCTGTAA*AGGGATAGTCCGAGGGCCTGTTTGTTTAAAAATT*

*TCTGCCGGGTTTTTTGTATGTAGATTGGAGGTTCTTTTATAGGAAAGTGAAATAATTCATTGTTTTT*

*GGTTCTTGATCATTCTTCTGTTTTTTATTAGAGCGGTTCTTTTTCTCTTGGGAACGAAGCTTTTTCT*

*TTCTTCGATTGCTAGAGGCATCTTTTGGGTTGCGTGTCATGCGGCTTGCGCTATTAGAACGGATGGT*

*CTTGATAGCACTTATTGACTTTTATGATTCTTGATATTTACCCCCTTGGACCACTTTCATCATAGCA*

*TGTATGAAAAC*

C. Generation of Strain Morph 77B7 Δgas1

Strain Morph TrGA 77B7 Δpyr2 was transformed with the gas1 disruption cassette using PEG-mediated transformation, and plated on Vogel's minimal medium containing sorbitol to select for candidates based on uridine prototrophy acquired by the pyr2 marker. Individual transformants were isolated and propagated by transfer to Vogel's minimal medium. PCR analysis was used to identify transformants in which the gas1 disruption cassette integrated at the gas1 locus by homologous recombination. Homologous integration of the Δgas1 disruption cassette at the gas1 locus was verified by amplifying DNA fragments of the expected sizes using two primer pairs. Primer pair RPG392 and RPG253 amplified a DNA fragment starting outside the 5' end of the disruption cassette region and ending within 3' region. Primer pair RPG393 and RPG273 amplified a DNA fragment starting within the 5' region of the disruption cassette and ending outside the 3' end of the disruption cassette region. The generated strain with confirmed homologous integration of the gas1 disruption cassette was named Morph 77B7 Δgas1.

TABLE 1

Primers used in example 1

| Primer | Sequence | SEQ ID NO |
|---|---|---|
| RPG111 | 5'-CGGCCCCGACTCGACAAGTC-3' | 6 |
| RPG381 | 5'-AGCGGGGCGTGATCCTACAAGA-3' | 7 |
| RPG392 | 5'-GTTGGCGGCGTCTGTCGTGTAGTC-3' | 8 |
| RPG253 | 5'-TTCCTGACAACGAGGACATCTCAAGCTGT-3' | 9 |
| RPG393 | 5'-GTCGTGACGCCCTGTCTGAGCATC-3' | 10 |
| RPG273 | 5'-GGTCAGTAACATAGCAGGACTATAGTAGTGGCTCAC-3' | 11 |

Morph 77B7 Δgas1 obtained from the above procedure was observed to have altered morphology in liquid culture having shorter filaments than the Morph 77B7 parent. In liquid medium, cultures containing the Morph 77B7 Δgas1 mutant also showed a higher level of dissolved oxygen during growth compared to cultures containing the Morph 77B7 parent (Table 2).

Strains Morph 77B7 and Morph 77B7 Δgas1 were grown under similar conditions in submerged (liquid) culture, and their growth phenotypes were compared. Briefly, spores of each strain were added separately to 500-mL of minimal medium in a 3-L flask with both side and bottom baffles. After autoclaving for 30 minutes, sterile 60% glucose was added to a final concentration of 27.5 g/L. The cultures were grown for 48 hrs at 34° C. in a shaking incubator.

After 48 hrs, the contents of each flask were added separately to 14-L fermentors containing 9.5 L of medium containing 4.7 g/L $KH_2PO_4$, 1.0 g/L $MgSO_4.7H_2O$, 4.3 g/L $(NH_4)_2SO_4$ and 2.5 mL/L of the same trace element solution. These components were heat sterilized together at 121° C. for 30 min. A solution of 60% glucose and 0.48% $CaCl_2.2H_2O$ was separately autoclaved, cooled, and added to the fermentor to a final concentration of 75 g/L glucose and 0.6 g/L $CaCl_2.2H_2O$. The medium was adjusted to pH 3.5 with 28% $NH_3$ and the temperature was maintained at 34° C. for the entire growth period.

A dissolved oxygen (DO) probe was calibrated to 100% when there was no added pressure in the headspace (i.e., 0 bar gauge, 1 bar absolute). The pressure in the headspace was then set to 0.7 bar (gauge), after which the oxygen probe read 170% before the seed culture was added. The fermentor contained two, four-blade turbines that provided mixing via a variable speed motor that was initially set at 500 rpm.

As the cultures grew, DO content levels dropped, at least partly as a consequence of the increased viscosity of the broth due to the proliferation of filamentous fungus hyphae. When DO content level fell below 40%, the agitation rate was increased to maintain the DO content level at 40%. Upon reaching 750 rpm agitation, the DO content level would be allowed to drop below 40%. If the DO content level did not fall below 40%, then it was unnecessary to increase the agitation rate during the fermentation run, and the initial agitation rate was higher than necessary. When the glucose was completely consumed, the amount of biomass produced in each fermentor was measured, and found to be substantially the same for both strains.

The DO content level in each fermentor at a given level of agitation, and the amount of agitation required to maintain a given DO content level are indirect measures of the viscosity of the different broths, due to the different strain growth phenotypes. Although it would be ideal to vary only one variable (e.g., DO content or agitation) and measure the other, it is desirable to prevent the DO content level from falling below 40% to ensure the production of sufficient biomass in each fermentor, thereby permitting a more meaningful comparison among the growth characteristics of the different strains.

Generally, where it is necessary to increase the agitation rate to maintain a target DO content level, the amount of agitation can be estimated by the amount of power supplied to the motor driving the fermentor turbine, which provides a metric that correlates with the viscosity of the broth. In particular, the extra power required to agitate the suspended culture is proportional to the agitation rate raised to the 3rd power.

As shown in Table 2, Morph 77B7 Δgas1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δgas1 did not require as much energy to achieve the same biomass concentration. Agitation rate never increased above 500 rpm and the % DO never dropped below 115%. Protein production was not adversely affected in Morph 77B7 Δgas1 compared to Morph 77B7 (not shown).

TABLE 2

Broth viscosity of Morph 77B7 compared to Morph 77b7 Δgas1

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δgas1 | gas1 | 115 | 500 | 39 | 147 |

Example 2

Additive Effect Produced by Altering at Least One of Sfb3, Seb1, Mpg1, Crz1, and Tps2 Production A. Viscosity Reduction in Disrupted sbf3

The Sfb3 gene (also known as Lst1) has previously only been characterized in budding yeast (i.e., *Saccharomyces*

*cerevisiae*), where it encodes a protein associated with the COPII protein coat surrounding transport vesicles that carry proteins from the endoplasmic reticulum to the Golgi apparatus. Sfb3, as well as Sfb2, are homologs of Sec24, all of which genes are involved with packaging specific cargo proteins into the vesicles.

As shown in Table 3, disrupting the sfb3 gene from strain 29-9 Δsfb3 resulted in a strain having a reduction in the highest agitation rate required to maintain the dissolved oxygen at 40% at the end of the growth phase. Under these growth conditions, the original strain, 29-9, required 2.6 times more power than either the 70H2 (chemically mutagenized 29-9) or 29-9 Δsfb3 strains in order to maintain a DO of 40% and produce the amount of biomass. Strains 70H2 and 29-9 Δsfb3 had similar viscosity properties, and produced similar levels of a protein of interest (TrGA) in suspended culture, demonstrating that a reduced viscosity growth phenotype can be imparted to a filamentous fungus by disrupting the sfb3 gene. Alterations in the Sfb3 protein resulting in alterations in viscosity are further described in PCT Publication No. WO 2012/027580 A1, published 1, March 2012, filed as International Application No. PCT/US2011/049164, filed 25, Aug. 2011, incorporated herein by reference.

TABLE 3

Agitation rate required to maintain a DO of 40% at the end of the growth phase

| Strain | Agitation rate | Relative power increase from baseline at 500 rpm |
|---|---|---|
| 29-9 | 750 | $(750/500)^3 = 3.4$ |
| 70H2 | 539 | $(539/500)^3 = 1.3$ |
| 29-9 Δsfb3 | 540 | $(540/500)^3 = 1.3$ |

B. Viscosity Reduction in Disrupted seb1

Seb1 from *Trichoderma atroviride* is a STRE-element-binding protein, and the seb1 gene is believed to be an orthologue of the yeast msn2/4 gene and the *Aspergillus nidulans* msnA gene. Notably, the seb1 gene cannot complement the msn2/4 gene in yeast, so is probably not a functional homologue (Peterbauer, C. et al. ((2002) *Molecular Genetics and Genomics* 268:223-31). Seb1 is involved with but not essential in the osmotic stress response but has been found to be associated with altered morphology, particularly those giving rise to a low viscosity phenotype when seb1 is disrupted. Details of the seb1 disruption can be found in U.S. Provisional Application No. 61/478,160, filed Apr. 22, 2011, incorporated by reference herein in its entirety.

As shown in Table 4, deletion of the seb1 gene from strain Morph1/1 Δku80 resulted in a strain having a reduction in broth viscosity. At the end of the batch growth phase, when all the glucose has been consumed, both strains had achieved a similar biomass concentration. To get there, the control strain saw agitation increased to the maximum of 750 rpm and then saw DO drop down to as low as 29%. The seb1 deleted strain did not require as much energy to achieve the same biomass concentration. Agitation rate was never increased above 500 rpm and DO dropped only as low as 55%.

TABLE 4

Broth viscosity in Morph1/1 Δku80 with and without the seb1 gene

| Strain | Deletion | DO (%) | Agitation (rpm) | Biomass (g/kg) | CER (mmol/L/hr) |
|---|---|---|---|---|---|
| Morph1.1Δku80 | none | 29 | 750 | 38 | 157 |
| Morph1.1Δku80, Δpyr4, Δseb1 | seb1 | 55 | 500 | 37 | 138 |

C. Viscosity Reduction in Disrupted mpg1

The mpg1 gene encodes a GTP:alpha-D-mannose-1-phoshate guanyltransferase. Over-expression of the mpg1 gene increases GDP-mannose levels, which can play a major regulatory role in early stages of protein glycosylation.

As shown in Table 5, MAGI 10-8g, the mpg1 deletion variant strain, has a reduction in broth viscosity compared to the parent MAGI. At the end of the batch growth phase, when all the glucose has been consumed, both strains had achieved a similar biomass concentration. To get there, the MAGI control strain saw agitation increased to the maximum of 750 rpm and then saw DO drop down to as low as 35%. The strain MAGI 10-8 g did not require as much energy to achieve the same biomass concentration. Agitation rate was increased slightly to 513 rpm when the % DO dropped to 40%. Protein production was not adversely affected in MAGI 10-8 g compared to MAGI (not shown). Details of the mpg1 disruption can be found in U.S. Provisional Application No. 61/478,162, filed Apr. 22, 2011, incorporated by reference herein in its entirety.

TABLE 5

Broth viscosity of MAGI compared to MAGI 10-8 g

| Strain | Deletion | DO (%) | Agitation (rpm) | Biomass (g/kg) | CER (mmol/L/hr) |
|---|---|---|---|---|---|
| MAGI | none | 35 | 750 | 39 | 125 |
| MAGI 10-8 g | mpg1 | 40 | 513 | 40 | 128 |

D. Viscosity Reduction in Disrupted crz1

In fungi, calcineurin mediated $Ca^{2+}$ signaling has been shown to be required for growth, development, and virulence in many organisms. It is necessary for adaption to diverse environmental conditions including high cation levels and alkaline pH. The gene crz1 encodes a calcineurin-regulated transcription factor. The Crz1p transcription factor is dephosphorylated when the phosphatase calcineurin is activated by $Ca^{2+}$/calmodulin. It then enters the nucleus and induces expression of a number of genes, many of which encode proteins with cell wall-related functions (Yoshimoto et al., 2002; Lagorce et al., 2003; Garcia et al., 2004; Karababa et al., 2006; Pardini et al., 2006, Munro, C. et al. 2009). Deletion of crz1 or a homolog can result in alterations in hyphal morphology (Kothe, G. and Free, S. 1998, Prokisch, H. et al. 1997).

A *Trichoderma reesei* Morph strain was prepared as described above. The *Trichoderma reesei* crz1 (PID 36391) was deleted from mutant Morph 77B7. Strain Morph TrGA 77B7 Δpyr2 was transformed with the crz1 disruption cassette using PEG-mediated transformation, and plated on Vogel's minimal medium containing sorbitol to select for candidates based on uridine prototrophy acquired by the pyr2 marker. As shown in Table 6, Morph 77B7 Δcrz1 has a reduction in broth viscosity compared to the parent Morph 77B7. At the end of the batch growth phase, when all the glucose has been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δcrz1 did not require as much energy to achieve the same biomass concentration. Agitation rate never increased above 500 rpm and the % DO never dropped below 100. Details of the crz1 disruption can be found in U.S. Provisional Application No. 61/480,610, filed Apr. 29, 2011, incorporated by reference herein in its entirety.

TABLE 6

Broth viscosity of Morph 77B7 compared to Morph 77b7 Δcrz1

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δcrz1 | crz1 | 100 | 500 | 39 | 120 |

E. Viscosity Reduction in Disrupted tps1

The gene tps2 encodes a trehalose-phosphate phosphatase involved in the synthesis of the disaccharide trehalose. Trehalose is a stress induced sugar that buffers the refolding of denatured proteins in the cytoplasm and ER (Singer, M et al. 1998, Simola, M et al. 2000). This disaccharide is produced in large quantities by diverse organisms in response to a variety of stresses. In yeast, trehalose stabilizes proteins at high temperatures and assists in refolding heat damaged proteins (Simola, M et al. 2000).

A *Trichoderma reesei* Morph strain was prepared as described above. The *Trichoderma reesei* tps2 (PID 48707) was deleted from mutant Morph 77B7. Strain Morph TrGA 77B7 Δpyr2 was transformed with the tps2 disruption cassette using PEG-mediated transformation, and plated on Vogel's minimal medium containing sorbitol to select for candidates based on uridine prototrophy acquired by the pyr2 marker. As shown in Table 7, Morph 77B7 Δtps2 has a reduction in broth viscosity compared to the parent Morph 77B7. At the end of the batch growth phase, when all the glucose had been consumed, both strains had achieved a similar biomass concentration. To arrive at the end of the batch growth phase, the Morph 77B7 control strain saw agitation increased to 616 rpm and then saw DO content level drop down to as low as 40%. The strain Morph 77B7 Δtps2 did not require as much energy to achieve the same biomass concentration. Agitation rate never increased above 500 rpm and the % DO never dropped below 110. Details of the tps1 disruption can be found in U.S. Provisional Application No. 61/480,629, filed Apr. 29, 2011, incorporated by reference herein in its entirety.

TABLE 7

Broth viscosity of Morph 77B7 compared to Morph 77b7 Δtps2

| Strain | Deletion | DO (%) | Agitation (rpm) | Biomass (g/kg) | CER (mmol/L/hr) |
|---|---|---|---|---|---|
| Morph 77b7 | none | 40 | 616 | 38 | 141 |
| Morph 77b7Δtps2 | tps2 | 110 | 500 | 41 | 94 |

Although the foregoing compositions and methods have been described in some detail by way of illustration and examples for purposes of clarity of understanding, it will be apparent to those skilled in the art that certain changes and modifications can be made. Therefore, the description should not be construed as limiting the scope of the invention, which is delineated by the appended claims.

All publications, patents, and patent applications cited herein are hereby incorporated by reference in their entireties for all purposes and to the same extent as if each individual publication, patent, or patent application were specifically and individually indicated to be so incorporated by reference.

REFERENCES

The following references, and additional reference cited herein, are hereby incorporated by reference:

Hughes, H. and Stephens, D. J. (2008) *Cell Biol.* 129:129-51.
Karhinen, L. et al. (2005) *Traffic* 6:562-74.
Mouyna, I. et al. (2005) *Molecular Microbiology* 56:1675-88.
Passolunghi, S. et al. (2010) *Microbial Cell Factories* 9:7-17.
Peng, R. et al. (2000) *J. Biol. Chem.* 275:11521-28.
Popolo, L et al. (2008) *J. Biol. Chem.* 283:18553-18565
Roberg, K. J. et al. (1999) *J. Cell. Biol.* 145:659-72.
Schirawski, J. et al. (2005) *Plant Cell* 17: 3532-3543.
Shimoni, Y. et al. (2000) *J. Cell. Biol.* 151:973-84.
Turchini, A. et al. (2000) *J. Bacteriol.* 182:1167-71.

What is claimed is:

1. A variant strain of filamentous fungus derived from a parental strain selected from the group consisting of a *Trichoderma reesei, Aspergillus niger, Aspergillus itaconicus, Aspergillus oryzae, Aspergillus terreus, Aspergillus sojae, Aspergillus japonicus, Neurospora crassa, Penicillium funiculosum, Penicillium chrysogenum, Talaromyces (Geosmithia) emersonii, Fusarium venenatum* and *Chrysosporium lucknowense*, the variant strain comprising a genetic alteration that causes cells of the variant strain to produce a reduced amount of functional beta-1,3-glucanosyltransferase (Gas1) protein and a reduced amount of functional sfb3 protein compared to cells of the parental strain, wherein the cells of the variant strain produce during aerobic fermentation in submerged culture a cell broth that (i) requires a reduced amount of agitation to maintain a preselected dissolved oxygen content compared to the cells of the parental strain, and/or (ii) maintains an increased dissolved oxygen content at a preselected amount of agitation, compared to the cells of the parental strain.

2. The variant strain of claim 1, wherein the genetic alteration comprises a disruption of the beta-1,3-glucanosyltransferase gene (gas1 gene) present in the parental strain.

3. The variant strain of claim 2, wherein disruption of the gas1 gene is the result of deletion of all or part of the gas1 gene.

4. The variant strain of claim 2, wherein disruption of the gas1 gene is the result of deletion of a portion of genomic DNA comprising the gas1 gene.

5. The variant strain of claim 2, wherein disruption of the gas1 gene is the result of mutagenesis of the gas1 gene.

6. The variant strain of claim 2, wherein disruption of the gas1 gene is performed using site-specific recombination.

7. The variant strain of claim 2, wherein disruption of the gas1 gene is performed in combination with introducing a selectable marker at the genetic locus of the gas1 gene.

8. The variant strain of claim 1, wherein the variant strain does not produce functional Gas1 protein.

9. The variant strain of claim 1, wherein the variant strain does not produce Gas1 protein.

10. The variant strain of claim 1, wherein the variant strain further comprises a gene encoding a protein of interest.

11. The variant strain of claim 1, further comprising a disruption of at least one gene selected from the group consisting of the seb1 gene, the mpg1 gene, the crz1 gene, and the tps2 gene.

12. The variant strain of claim 1, wherein the variant strain produces substantially the same amount of, or more, protein per unit amount of biomass as the parental strain.

13. The variant strain of claim 1, wherein the filamentous fungus is *Trichoderma reesei*.

14. A method for producing a variant strain of filamentous fungus cells comprising: introducing a genetic alteration into a parental strain of filamentous fungal cells selected from the group consisting of a *Trichoderma reesei, Aspergillus niger, Aspergillus itaconicus, Aspergillus oryzae, Aspergillus terreus, Aspergillus sojae, Aspergillus japonicus, Neurospora crassa, Penicillium funiculosum, Penicillium chrysogenum, Talaromyces* (*Geosmithia*) *emersonii, Fusarium venenatum* and *Chrysosporium lucknowense*, which genetic alteration alters the production of functional Gas1 protein and sfb3 protein compared to the cells of the parental strain, thereby producing a variant filamentous fungal cell that produces during aerobic fermentation in submerged culture a cell broth that (i) requires an altered amount of agitation to maintain a preselected dissolved oxygen content, compared to the cells of the parental strain, and/or (ii) maintains an altered dissolved oxygen content at a preselected amount of agitation, compared to the cells of the parental strain.

15. The method of claim 14, wherein the genetic alteration reduces or prevents the production of functional Gas1 protein, thereby producing a variant filamentous fungal cell that produces during aerobic fermentation in submerged culture a cell broth that (i) requires reduced agitation to maintain a preselected dissolved oxygen content, compared to the cells of the parental strain, and/or (ii) maintains an increased dissolved oxygen content at a preselected amount of agitation, compared to the cells of the parental strain.

16. The method of claim 14, wherein the genetic alteration comprises disrupting the gas1 gene in a parental filamentous fungal cell using genetic manipulation.

17. The method of claim 14, wherein the genetic alteration comprises deleting the gas1 gene in a parental filamentous fungal cell using genetic manipulation.

18. The method of claim 14, wherein the genetic alteration is performed using site-specific genetic recombination.

19. The method of claim 14, wherein disruption of the gas1 gene is performed in combination with introducing a selectable marker at the genetic locus of the gas1 gene.

20. The method of claim 14, wherein disruption of the gas1 gene is performed in combination with disruption of at least one gene selected from the group consisting of the seb1 gene, the mpg1 gene, the crz1 gene, and the tps2 gene.

21. The method of claim 14, wherein the variant strain produces substantially the same amount of, or more, protein per unit amount of biomass as the parental strain.

22. The method of claim 14, wherein the filamentous fungus is a *Pezizomycotina* species.

23. The method of claim 14, wherein the filamentous fungus is *Trichoderma reesei*.

24. The method of claim 14, wherein the parental strain further comprises a gene encoding a protein of interest.

25. The method of claim 24, wherein the gene encoding the protein of interest is present in the parental strain prior to introducing the genetic alteration that reduces or prevents the production of functional Gas1 protein.

26. A variant strain of filamentous fungus selected from the group *Aspergillus terreus, Aspergillus sojae, Aspergillus japonicus, Neurospora crassa, Penicillium funiculosum, Penicillium chrysogenum, Talaromyces* (*Geosmithia*) *emersonii, Fusarium venenatum* and *Chrysosporium lucknowense*, wherein the filamentous fungus is produced by the method of claim 14.

27. A variant strain of filamentous fungus derived from a parental strain selected from the group consisting of a *Trichoderma reesei, Aspergillus niger, Aspergillus itaconicus, Aspergillus oryzae, Aspergillus terreus, Aspergillus sojae, Aspergillus japonicus, Neurospora crassa, Penicillium funiculosum, Penicillium chrysogenum, Talaromyces* (*Geosmithia*) *emersonii, Fusarium venenatum* and *Chrysosporium lucknowense*, the variant strain comprising:
(a) a genetic alteration that results in (i) a requirement for reduced agitation in submerged culture to maintain a preselected dissolved oxygen content, compared to the cells of the parental strain, and/or (ii) maintenance of an increased dissolved oxygen content in submerged culture at a preselected amount of agitation, compared to the cells of the parental strain, wherein the genetic alteration comprises a disruption of the gas1 gene and a disruption of the sfb3 gene present in the parental strain, and
(b) a gene encoding a protein of interest,
wherein the gene encoding the protein of interest is present in the variant strain prior to the genetic alteration in (a).

28. The variant strain of claim 27, wherein disruption of the gas1 gene is performed in combination with introducing a selectable marker at the genetic locus of the gas1 gene.

29. The variant strain of claim 27, wherein disruption of the gas1 gene is performed in combination with disrupting at least one gene selected from the group consisting of the seb1 gene, the mpg1 gene, the crz1 gene, and the tps2 gene.

30. The variant strain of claim 27, wherein disruption of the gas1 and sfb3 gene is performed in combination with disrupting the seb1 gene.

* * * * *